(12) United States Patent
Johnson et al.

(10) Patent No.: US 9,785,744 B2
(45) Date of Patent: Oct. 10, 2017

(54) SYSTEM AND METHOD FOR PROTOCOL ADHERENCE

(75) Inventors: Christopher Donald Johnson, Clifton Park, NY (US); Peter Henry Tu, Niskayuna, NY (US); Piero Patrone Bonissone, Schenectady, NY (US); John Michael Lizzi, Jr., Wilton, NY (US); Kunter Seref Akbay, Niskayuna, NY (US); Ting Yu, Albany, NY (US); Corey Nicholas Bufi, Troy, NY (US); Viswanath Avasarala, Schenectady, NY (US); Naresh Sundaram Iyer, Saratoga Springs, NY (US); Yi Yao, Rexford, NY (US); Kedar Anil Patwardhan, Latham, NY (US); Dashan Gao, Rexford, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 570 days.

(21) Appl. No.: 13/231,639

(22) Filed: Sep. 13, 2011

(65) Prior Publication Data
US 2012/0154582 A1    Jun. 21, 2012

Related U.S. Application Data

(60) Provisional application No. 61/382,708, filed on Sep. 14, 2010.

(51) Int. Cl.
*H04N 7/18* (2006.01)
*G06F 19/00* (2011.01)
(Continued)

(52) U.S. Cl.
CPC .......... *G06F 19/327* (2013.01); *G06F 19/321* (2013.01); *G06F 19/3418* (2013.01); *G06Q 10/00* (2013.01); *G08B 21/245* (2013.01)

(58) Field of Classification Search
CPC .. G06F 19/321; G06F 19/327; G06F 19/3418; G06Q 10/00
(Continued)

(56) References Cited

U.S. PATENT DOCUMENTS 7,567,697 B2   7/2009  Mostafavi
7,586,413 B2   9/2009  Davis
(Continued)

FOREIGN PATENT DOCUMENTS

CN      1953426 A      4/2007
WO   2007129289 A1   11/2007
(Continued)

OTHER PUBLICATIONS

Jin, "People Location and Orientation Tracking in Multiple Views," IEEE, pub. 2009.*
(Continued)

*Primary Examiner* — Andy Rao
(74) *Attorney, Agent, or Firm* — Hanley, Flight and Zimmerman, LLC

(57) ABSTRACT

The system and method disclosed herein provides an integrated and automated workflow, sensor, and reasoning system that automatically detects breaches in protocols, appropriately alarms and records these breaches, facilitates staff adoption of protocol adherence, and ultimately enables the study of protocols for care comparative effectiveness. The system provides real-time alerts to medical personnel in the actual processes of care, thereby reducing the number of negative patient events and ultimately improving staff behavior with respect to protocol adherence.

20 Claims, 20 Drawing Sheets

(51) Int. Cl.
*G06Q 10/00* (2012.01)
*G08B 21/24* (2006.01)

(58) Field of Classification Search
USPC .................................. 348/521, 77, 143–160
See application file for complete search history.

(56) References Cited

U.S. PATENT DOCUMENTS

| | | | |
|---|---|---|---|
| 8,085,302 B2* | 12/2011 | Zhang et al. | 348/169 |
| 8,319,635 B2 | 11/2012 | Perkins et al. | |
| 8,334,906 B2* | 12/2012 | Lipton et al. | 348/169 |
| 8,457,656 B2 | 6/2013 | Perkins et al. | |
| 8,712,330 B2 | 4/2014 | Desai et al. | |
| 8,762,519 B2 | 6/2014 | Thomson et al. | |
| 8,847,754 B2 | 9/2014 | Buchheim et al. | |
| 8,849,754 B2 | 9/2014 | Craggs | |
| 8,948,782 B2 | 2/2015 | Shang et al. | |
| 9,031,577 B2 | 5/2015 | Mirzaei et al. | |
| 9,277,018 B2 | 3/2016 | Kotecha et al. | |
| 9,374,667 B1 | 6/2016 | Jorgensen et al. | |
| 2002/0183979 A1* | 12/2002 | Wildman | 702/188 |
| 2005/0105765 A1* | 5/2005 | Han et al. | 382/100 |
| 2005/0116821 A1 | 6/2005 | Wilsey et al. | |
| 2006/0173936 A1* | 8/2006 | Castro et al. | 707/205 |
| 2007/0011125 A1* | 1/2007 | Angele | G06N 5/045 706/46 |
| 2008/0199155 A1 | 8/2008 | Hagens et al. | |
| 2009/0087028 A1 | 4/2009 | Lacey et al. | |
| 2009/0089093 A1 | 4/2009 | Johnson et al. | |
| 2011/0001605 A1* | 1/2011 | Kiani et al. | 340/5.6 |

FOREIGN PATENT DOCUMENTS

| | | |
|---|---|---|
| WO | 2008100832 A1 | 8/2008 |
| WO | 2009049038 A1 | 4/2009 |
| WO | 2010102069 A2 | 9/2010 |

OTHER PUBLICATIONS

Hanson ("The Bayes Inference Engine," I Maximum Entropy and Bayesian Methods, pp. 125-134, Luwer Academic, Dordrecht, 1996).*

"Spot by InnerWireless: A Rational Solution for Healthcare Asset Tracking," 1155 Kas Drive, Suite 200, Richardson, 75081; http://www.innerwireless.com, pp. 1-8.

Search Report and Written Opinion from corresponding PCT Application No. PCT/US2011/051510 dated Nov. 10, 2011.

Ji Tao et al., "Fall Incidents Detection for Intelligent Video Surveillance", Information, Communications and Signal Processing, 2005 Fifth International Conference on Bangkok, Thailand Dec. 6-9, 2005, Piscataway, NJ, USA,IEEE, Piscataway, NJ, USA, Dec. 6, 2005, pp. 1590-1594.

Translation of CN office action issued on Mar. 2, 2015 in relation to corresponding CN application 201180054809.7.

Yang Lei, "Research for Abnormal Detection Program in Intelligent Monitoring System of Empty Nesters," China's Outstanding Master Degree Dissertation Full—text Database Information Technology Series, Apr. 15, 2010; vol. 4, China Academic Journal (CD) electronic magazine, Beijing, China.

Tao et al, "Fall Incidents Detection for Intelligent Video Surveillance," 2005, pp. 1590-1594, School of Electrical & Electronic Engineering, Nanyang Technological University, Signapore.

* cited by examiner

SYSTEM AND METHOD FOR PROTOCOL ADHERENCE

CROSS-REFERENCE TO RELATED APPLICATIONS

This application claims the benefit of U.S. Provisional Patent Application No. 61/382,708, entitled "System and Method for Protocol Adherence," and filed Sep. 14, 2010, which is herein incorporated by reference in its entirety for all purposes.

BACKGROUND

Protocol-centric environments are institutions such as hospitals, step down facilities, nursing and private homes, and the like. A hospital is used herein as an example of a protocol-centric environment. Adverse events that occur in hospitals, such as, for example, hospital-acquired infections, result in patient harm, increased recovery time, unreimbursed healthcare costs, and loss of a hospital's and its staff's capacity to serve. One of the main causes of these events is non-adherence to protocols. As used herein, protocols refer to a series of preferred or prescribed tasks that (1) have been proven to reduce adverse events and (2) effect a desired elimination of activities, practices, or patterns that create harm or inefficiency. Example uses of such protocols are for hand washing, fall prevention, rounding, pain management, sleep improvement, pressure ulcer prevention, and tube management (ventilator, urinary tract, and central line being examples).

As an illustrative example, despite widespread knowledge that proper hand washing reduces pathogen transmission, adherence by visitors of patients under an infection control protocol and even hospital staff can remain low with mean baseline rates of routine compliance across organizations ranging from approximately 5%-81%, with an overall compliance of approximately 40%. While there are many reasons for non-compliance (including a perceived lack of risk, time to wash, missing knowledge of protocol, or associated discomfort from complying with protocol and general inconvenience) improvement in hand sanitization before coming in contact with patients and often upon completing contact, will reduce the spread of bacteria and thus lower the incidence of adverse events, thereby improving the standard of care. It is therefore advantageous to help the providers of healthcare and other persons involved in a patient's care or visitation to comply with protocols.

Many procedures benefit from a higher frequency of protocol compliance. Even relatively low level and treatable infections, such as a urinary tract infection, can escalate to life-threatening conditions including sepsis. Protocols to change tubes, if followed, will reduce the incidence of opportunities leading to infection onset. Other care plans, such as those for ventilators have associated protocols, which if followed, also reduce adverse events. Mortality rates for ventilator associated pneumonia that can be attributed to breaches in patient position and ventilator tube changing protocols, range from approximately 25%-50% and can reach up to 76% in specific settings. Estimates of the costs for one case of ventilator-associated pneumonia have been reported to be $10,000-$16,000 adding an estimated 4-32 additional ventilator days. Harm is therefore inflicted on the patient and a healthcare institution's ability to serve is diminished.

Systems that have been developed to track and analyze activities in a clinical setting have focused primarily on single modality sensing, for example, Radio Frequency Identification (RFID) or infrared (IR) or manual key input or written bed board updates or human observatory monitoring schemas. As an example, one known RFID-based system focuses on identifying human activities in a hospital environment using Hidden Markov Models (HMMs) for supporting context aware applications. While some manufacturing systems may incorporate a combination of RFID and computer vision, the multiple sensors are used to produce a discrete snapshot in time and does not provide contextual information over a period of time.

Typically, RFID sensor systems take the form of location and contact make/break sensing systems for certain protocol adherence. As one example, an institution may specify that staff shall sanitize their hands upon entrance into the patient's room. Since there is little or no mechanism to reason what the staff is doing in the room or context, simple non-nuanced standing procedures are enforced. Sensor systems such as those that are IR or RFID-based determine if staff was in the presence of a hand sanitization station, or if cleansing agents are dispensed. A process defect is alarmed or recorded when staff enter a room and do not sanitize. In other systems, the provider of care wears a device to display they have hand sanitized but partially leave the protocol adherence determination to the patient for warning the care provider.

In non-healthcare domains, such as commercial shopping monitoring, humans in effect become the sensors with such programs as 'secret shoppers' and behavioral studies that use shopping patterns to infer consumer propensities to select product preferentially.

However, in such single modality systems a sensor must be associated with the patient, care provider, or apparatus being monitored. Further, such systems do not provide information regarding whether specific behaviors and actions are occurring according to specified temporal-spatial relationships nor do such systems provide in-situ feedback and/or contextually appropriate workflow and/or insightful summary reporting. RFID systems are further limited by their range; typically RFID systems have a tolerance of approximately plus-or-minus 10 feet.

In systems that employ optical sensing, optical tags may be used to identify objects such as specific equipment, patients, care providers, and sundry apparatus. Such systems typically provide optical or other tag information to a video record, may superimpose such information on a display, or may identify the orientation of a plurality of reference points for optical positioning for the purposes of diagnostic imaging or placement of apparatus such as biopsy needles.

The University of Pittsburgh Medical Center has pilot tested a concept of a Smart Room, which includes the integration of speech recognition, ultrasound, and electronic health record data, to support some patient safety and clinical information sharing. However, such system is limited in the number of sensing systems that it employs and uses data from the sensing systems to access appropriate data to post on computer screens in a patient's room. Thus, the system does not provide any contextual meaning to feedback received from the sensors.

Known systems also incorporate a sensor-based system for monitoring caregiver performance focused on avoiding pressure ulcers in patients. However, the sensors such systems typically employ do not monitor position latency, velocities, momentum, or the contextual state of other items that contribute to pressure ulcer formation such as the actions of caregivers and cumulative movements of the patient relative to the desired.

Therefore, it would be desirable to design a system and method for protocol adherence.

BRIEF DESCRIPTION OF THE DRAWINGS

The drawings illustrate preferred embodiments presently contemplated for carrying out the invention.

In the drawings.

DETAILED DESCRIPTION

Figure 1:
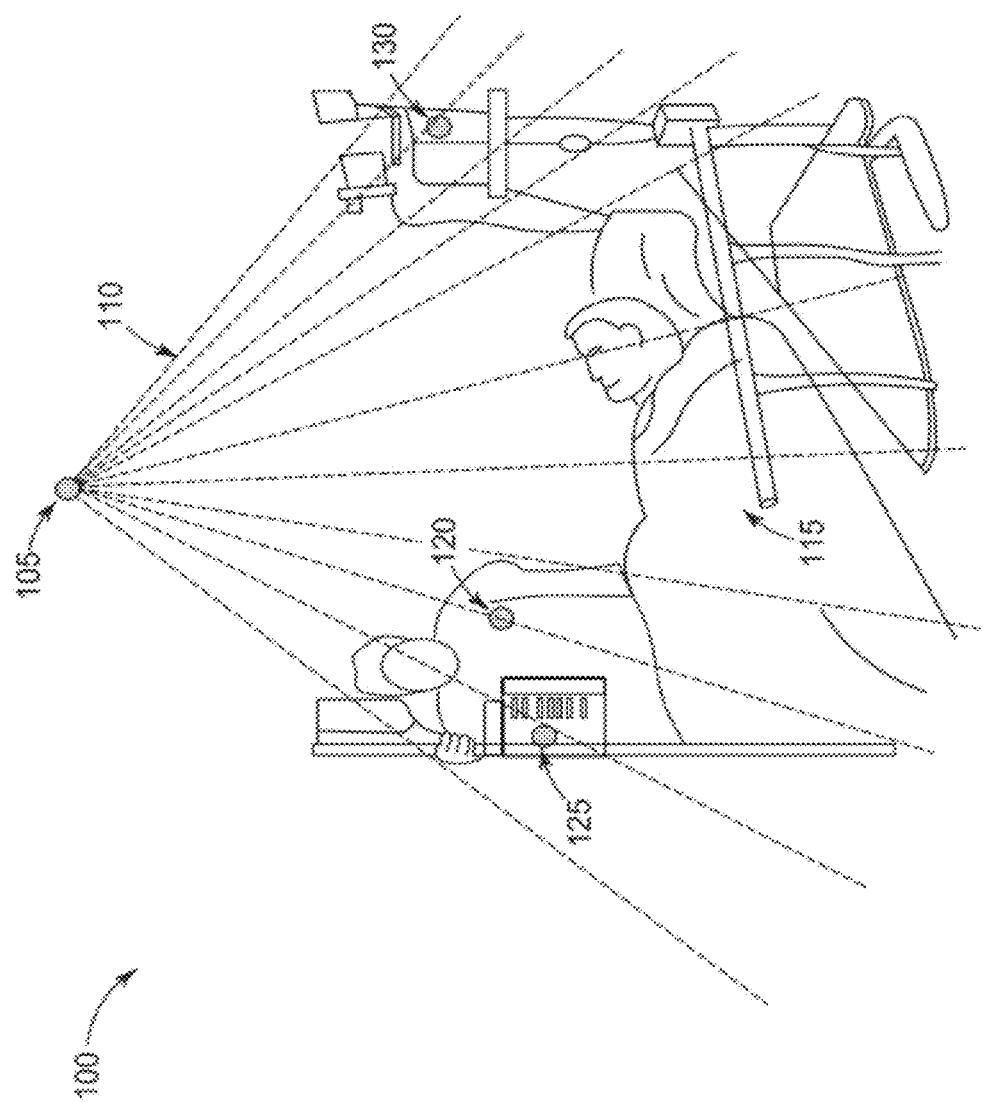
FIG. 1 is a schematic of an exemplary protocol adherence system, in accordance with an embodiment of the invention.

The system and method disclosed herein provides an integrated and automated workflow, sensor, and reasoning system that automatically detects breaches in protocols, appropriately alarms and records these breaches, facilitates staff adoption of protocol adherence, and ultimately enables the study of protocols for care comparative effectiveness. The system provides real-time alerts to medical personnel in the actual processes of care, thereby reducing the number of negative patient events and ultimately improving staff behavior with respect to protocol adherence.

An optically based sensor system is deployed that determines the location and trajectory of people as well as the presence of certain objects and settings or status of configured apparatus, which singularly or in conjunction with other analog and digital data, informs a reasoning engine that calculates the state of the monitored people and objects. Deviations from desired states are determined and appropriate reporting and alarming is made. The sensor and reasoning systems are hosted in a message brokered computing environment that may persist in one or more computers and locations.

A goal of the disclosed system is to modify the behavior of medical staff and visitors with respect to patient care quality. Humans cannot multitask beyond a certain point. As such, reminders as to proper protocols can prevent situations that will ultimately lead to quality of care degradation. To this end, the system will continually monitor patient room activity with the intent of detecting and/or predicting breaches with respect to a specified set of protocols. As used herein, "protocols" refer to an ordered sequence of events or tasks or motions, events or tasks with deterministic or conditional path dependence or checklists that may or may not have an ordered temporal or spatial preference. In the healthcare example, protocols include policy, tasks, clinical events, regulatory events, administrative events specified for the care of patients. Such protocols may, as examples, include hand washing before and after interacting with a patient, monitoring rounds of care givers, monitoring physical activity of patients, monitoring patient positions and making sure that patients, especially sedentary ones, are turned on a regular basis so as to prevent the occurrence of pressure ulcers, cleaning protocols, and scheduling protocols. Embodiments of the invention may be used in training, in-situ monitoring, to record events and state changes in other systems such as medical event reporting or bed boards or the system's own activity record.

Examples set forth herein focus on the monitoring of tasks, which are specified a-priory, that comprise a protocol using information from databases, sensor systems, motion and optical shape recognition in the healthcare clinical services delivery venue. This system captures inputs or state changes from the art of computer vision object, movement and persons identification, telemetry signal processing, sensor systems and electronic records in order to uniquely reason or identify the state of activities being monitored relative to prescribed protocols. The ability to uniquely identify an entity is achieved by temporal and spatial patterns, observed people and device geometries, either or both of targets or shapes and in conjunction with optical beaconing or radio frequency identification. The ability to transform state space information into decision support that can be acted upon is derived from the disclosed system's workflow logic. The workflow configuration, interdependencies and specification, sensing, reasoning of state space and alerting or reporting are implemented on computer systems using computer code on single or networked devices.

While the detailed description focuses on "medical staff," "care provider," and "stakeholder," a skilled artisan will recognize that the system and method may be applied to any person interacting with the patient, including visitors as an example. Further, while the system and method set forth herein is described with respect to a healthcare clinical process, it can be readily appreciated that the system and method is equally applicable to other human process activities that involve humans and protocols to achieve objectives, such as, for example, manufacturing, food preparation, apparatus service, training, customer service, security, etc.

Embodiments of the invention depart from the current methods and systems in a number of ways. For example, embodiments include a real time system comprising software and hardware modules that are integrated into real-time hospital operational workflow and work together to understand activities in a monitored environment, determine whether the activities conform to explicit or implicit protocols, and to automatically tailor communication (i.e., message, channel, and intensity) to change behavior that results in adverse events. In "closing the protocol loop," the tasks can be accurately monitored and feedback provided both directly on the prescribed protocol as well as for pattern discovery. Accordingly, embodiments may be used to improve the patient flow, maximize staff utilization, minimize unnecessary length of stay, and ultimately, improve the financial sustainability of the overall hospital system. Success for the system implies an improvement of medical staff and visitor behavior with regard to such protocols after a certain period of use, thus resulting in fewer adverse medical events and/or negative patient outcomes (e.g., infection, falls and pressure ulcers).

Embodiments include a number of key continuous functions, including care plans that invoke protocols and sub tasks that must be executed and transform the protocols into time, space, and resource ordered tasks that are queued for monitoring. Also, a combination of multi-modal sensors and computer vision is used to identify motion, objects, and people alone or in combination with data and traditional sensor inputs and analyze activity analysis (i.e., through reasoning over 1 or more sensor signals). A reasoning engine is then used to determine the state of the systems and tasks related to the protocols. Such combination may include the use of telemetry, computer vision, RFID, audio analysis, commercial sensor technology, and the like, as described in detail below.

The reasoning engine may be used, for example, for anomaly detection (e.g., "agent A is violating protocol task X"). In addition, embodiments dynamically direct workflow in such a way as to minimize adverse events and overall process flow constraints. Accordingly, embodiments of the disclosed system may be used to minimize adverse events in protocol-centric environments, such as breaches in patient care protocols, infections, falls, and other hospital-acquired conditions, thereby reducing patient harm.

Further, embodiments disclosed herein form a system of systems that enable discrete and corporate response via the use of message brokering to facilitate a multitude of sensors, algorithms, and computing infrastructure.

Accompanying this technology is a comprehensive human motivational method that facilitates the building of a shared vision for dramatically reducing the lapses in protocol adherence that contributes to adverse events. This is facilitated by the impartial, continuous fact-based feedback which the disclosed provides. For example, embodiments present fact-based feedback to humans for contextual feedback for the purposes of professional development and behavioral change influencing (e.g., real-time audible notification, post-event aggregation, analysis, and reporting, etc.). Where clinical care adverse medical event reduction, behavioral change, and skill building is a focus, a means to monitor the delivery of proper protocol steps and provide real time guidance relative to the desired protocol will improve the consistency of medical care and improve medical staff behavior with respect to protocol adherence.

Accordingly, the system and method disclosed herein manages the clinical workflow of delivering appropriate protocols, unobtrusively monitors the associated steps, determines if the care is being delivered within the specified clinical practice guidelines, and alerts providers to lapses of procedure.

FIG. 1 illustrates a schematic of an exemplary protocol adherence system, in accordance with an embodiment of the invention. People, objects, motion, and visual signals such as displays, coupled with other data from various systems are acquired for the purposes of determining what the state of the environment (the system and its stakeholders) is relative to the tasks of a protocol. A schema 100 for the protocol adherence system is shown in FIG. 1, with particular emphasis on the optical sensing aspect.

A computer vision system, which includes sensor 105, is utilized to acquire images that are then reasoned over to ascertain what the objects are in those images. The computer vision system transforms the representation into mathematical vector space where in those vectors are transformed into positional meaning, such as the location of a person. Thus, objects may be ascertained without a physical reproduction or display of an image.

According to one embodiment, sensor 105 is an optical sensor that is in such a way as to have line of sight 110 to the objects, patients 115, and various activities of interest, such as hand washing as an example. For precise identification of things, an optical pattern may be affixed to clothing 120, tags 125, or devices 130. Optical sensor 105 may be used to identify object and static patterns on such devices as tags as well as to read dynamic signals produced on the displays of devices 125 and 130 such as, for example an EKG, a specific ventilator tube, a specific medication, or a specific dressing, or other clinical devices producing graphs, status lights, and physical settings such as knob position. These optically discernable patterns are beneficial when the shape of an object is similar one to another yet it is desirous to know what the specific object it is. Non-clinical devices may also be monitored such as bed rails and their position, motion in zones within the monitored areas, and the like. Further, the optical sensors may read the screens of clinical devices and other screens of sundry devices. Outputs from optical sensor 105 are received by a reasoning engine, described in detail below, which will ingest messages emanating from the optical sensing system.

Figure 4:
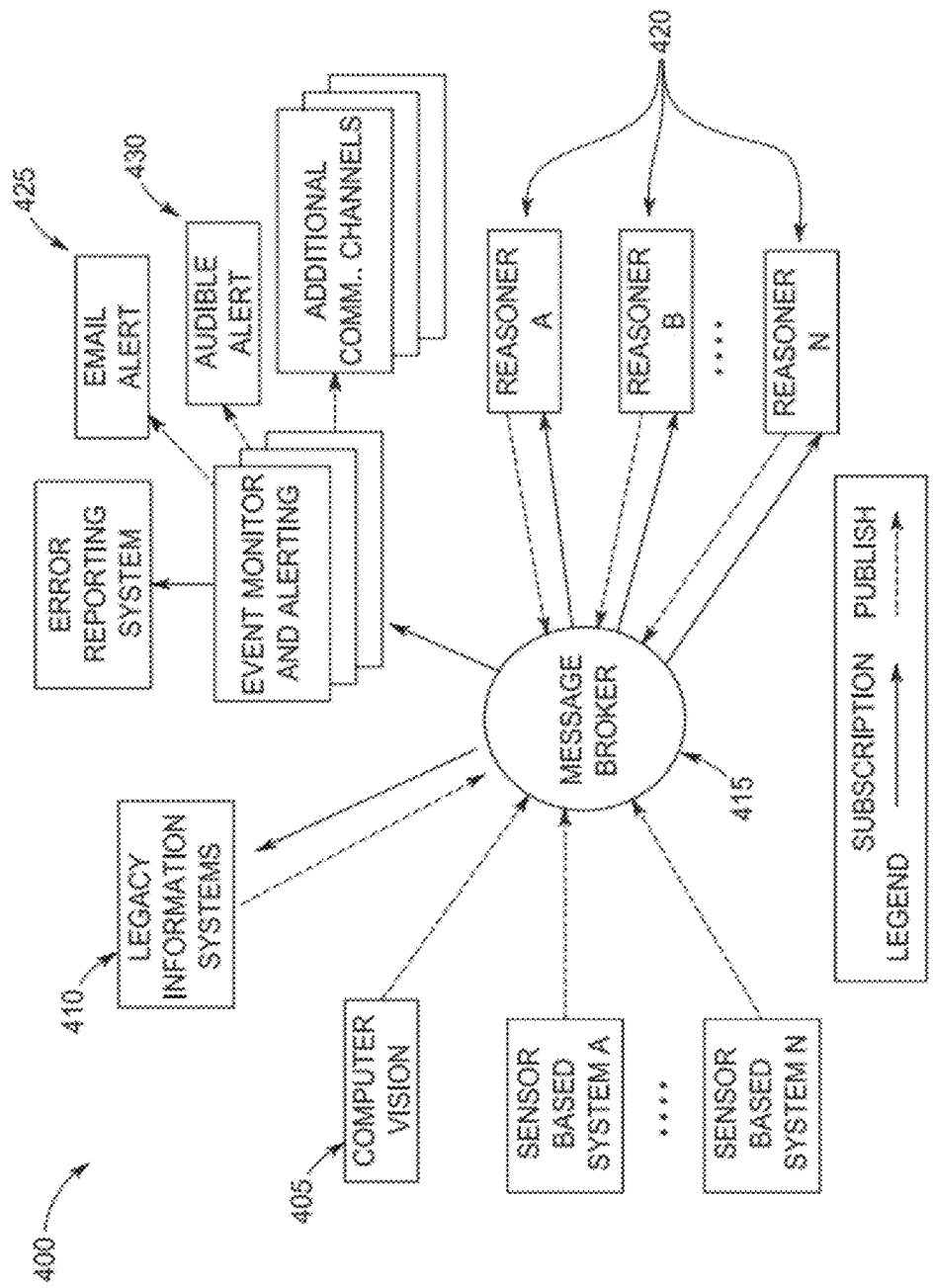
FIG. 4 is a schematic of a high level design of a protocol adherence system according to an embodiment of the invention.

The set-up of a room may also be derived from the optical system using its ability to discern objects and patterns. An example would be that a patient's torso is elevated, the bed height is of a certain length to the floor, that certain objects such as telephone, food tray or clinical systems are positioned, as they should be per the monitored hospital protocols. Accordingly, optical sensor 105 may be used to monitor a care provider with optical tag 120 who is in the room to set the patient 115 for minimum fall risk. Tasks to achieve the protocol may include setting the bed height below a certain distance to the floor. The same information that care provider 120 is in the room may be repurposed by other monitored protocols, such as, for example, ventilator-acquired pneumonia prevention or rounding. The optical sensing 105 system employs computer vision and publishes a message to a message broker system, such as system 400 (FIG. 4). Such message may include information that the care provider tagged as 120 is present and may be subscribed to by multiple protocol monitoring engines.

By providing a plurality of optical sensors 105 positioned throughout the room, spatial differentiation and occluded scenes of interest cause by interruptions in line of site 110 may be overcome. As such, system 100 includes a predetermined number of sensors to establish a continuous line of sight 110 and robust tracking of patients, caregivers, and objects within the patient's room. Accordingly, any desired level of optical precision to discern objects or attributes of the objects may be accommodated.

According to one embodiment, optical sensor 105 is adjustable such that it may be directed in various directions. As one example, the direction of adjustable sensor 105 is a pantel-zoom camera and is controlled by pantel-zoom manipulation by reasoning logic in which the degree of certainty of the state space is not as high as desired and a level of certainty on determination is higher. The set point level of desired precision itself may be adjustable based upon the patterns or instantaneous state of the monitored entities and events.

The use of optical sensor 105 to locate and/or identify people, objects, and motion may beneficially replace or augment other location sensing apparatus such as RFID, Doppler, LIDAR, and/or infrared. The optical sensing may be in the visible and/or invisible light range such as, for example, near IR. The sensing device 105 may be pixilating device, such as, for example, a video camera or a 3-D radar device producing direct vector length outputs. According to one embodiment, range radar and/or lidar signals may be used in conjunction with computer vision systems to acquire positional information in low light environments.

In addition, the optical sensing 105 may be used to adjust the light levels in the room sufficient to achieve requisite illumination for detection. The same system may be used to adjust lighting levels on an ongoing basis such as, for example, energy reduction when ambient lighting levels from windows provide light or in response to a command to lower energy consumption. Further, therapeutic uses of light color, level, or patterns may also be controlled by the sensing system in an adaptive way, in response to a protocol or set point or response of the patient.

Sensing uses of light absorption may also be used for measuring purposes. Heat changes detected in the patient 115 or equipment have context that the disclosed uses to improve the robustness of care delivery. Thermal sensors may be used as part of the invention to sense flight/fight response to stimuli as well as skin or bandage or device temperature on a relative or absolute bases and to consume this sensor information in the system's reasoning capability.

While system 100 is described as including an optical sensor 105, one skilled in the art will recognize that any combination of sensing modalities may be employed in system 100, such as, for example, other location sensing apparatus such as RFID, Doppler, LIDAR, infrared IR pulses, and/or other modes of object shape recognition.

Figure 2:
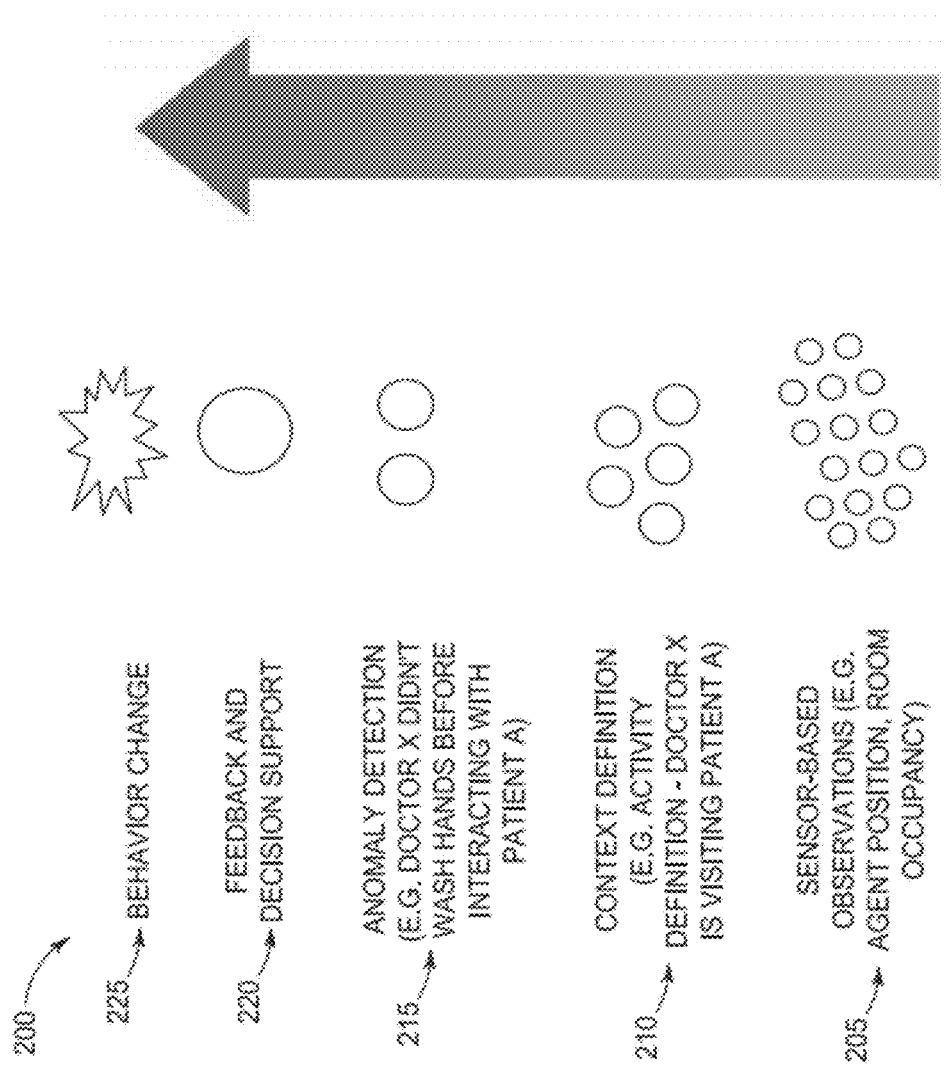
FIG. 2 illustrates a hierarchy of reasoning and decision support, in accordance with an embodiment of the invention.

The disclosed system and method reduces adverse events in processes by intervening into the process tasks as they are executed and enabling behavioral change by providing objective, contextual data to the stakeholders in the processes in either or both near real time or post activity. Accordingly, FIG. 2 illustrates a system 200 for a hierarchy of reasoning and decision support, in accordance with an embodiment of the invention.

In processes that rely on behavior, both real time interventions when tasks are not being performed to minimum specification as well as summary reporting must be accurately and contextually provided. Further, false interventions and overall conclusions must be avoided so as to build trust sufficient for behavioral change by self-determination of the individual healthcare providers. The strategic intent of embodiments of the system disclosed herein is that people will choose to improve if they trust the provided decision support and its objective feedback.

System 200 includes various discrete sensors 205 such as, for example, camera, video, infrared, load cells, telemetry, and data from adjacent systems that is used to transform raw observations into context definition 210 of what is transpiring in the monitored environment. By comparing what is occurring to what is desired to occur (i.e., the monitored state with the desired state), anomalies 215 are produced that indicate a deviation from what is desired. These anomalies may or may not be acted upon. The beneficial logic of the disclosed system determines which anomalous behavior can or should be acted upon 220 by those directed to or are able to act.

Over a number of observations, patterns emerge that can be used to beneficially inform stakeholders in the monitored process. For example, patterns may be used for positive reinforcement or to help highlight specific areas and contexts where task execution enhancement will better achieve the desired states of the system. Adherence to protocol may be achieved by the stakeholders in the processes of care choosing themselves to personally and closely follow guidelines or adherence to protocol. This may be achieved as a result of the provided in-situ feedback alerting a stakeholder of a variance to which they would respond appropriately to (or have performance consequences) and/or the provided objective feedback. By informing stakeholders of these patterns, stakeholders are encouraged to proactively change their behavior in such a way as to avoid the anomaly all together. Accordingly the observations may be used to transform stakeholder behavior 225 in such a way as to avoid having protocol violations or adverse states of the system.

Figure 3:
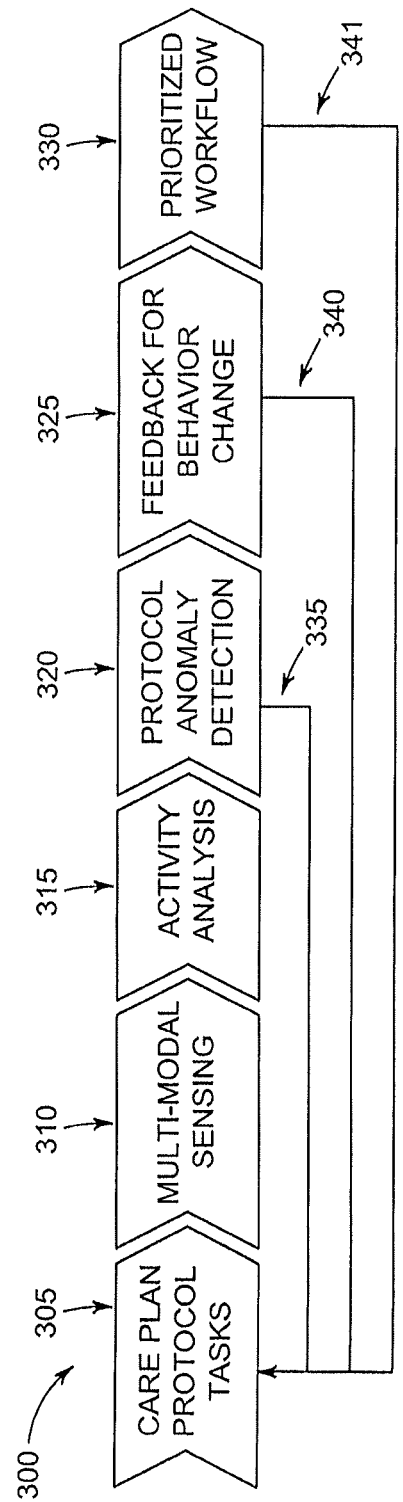
FIG. 3 is a flow chart illustrating continuous functions of a protocol adherence system according to an embodiment of the invention.

FIG. 3 is a flow chart illustrating continuous functions of a protocol adherence system 300, according to an embodiment of the invention. Six major continuous components enable the transformation of desired protocol execution to active workflow intervention and various reporting/feedback means. The six key continuous functions of system 300 are: Care Plan Protocol Tasks 305; multi-modal sensing 310 (e.g., through Computer Vision, RFID, audio analysis; commercial sensor technology, etc.); activity analysis 315 (i.e., through reasoning over 1 or more sensor outputs in the instant of time or over multiple time intervals); Protocol Anomaly Detection 320 (e.g., "agent A is violating protocol X"); and feedback for behavior change 325 (e.g., real-time audible notification, post event aggregation, pattern detection and reporting, etc.). Embodiments of the invention may incorporate one, all, or any combination of the six key continuous functions 305, 310, 315, 320, 325, and 330 and an ever-expanding universe of protocols that can be accurately managed.

Certain care plans are determined as appropriate and desirable for the patient. The first continuous function 305 is illustrated upon admittance to the institution or as prescribed by a healthcare professional when extending the monitoring of protocols to other venues such as the home. Within care plans, there are typically protocols of care that have been found to be advantageous for treating medical conditions or accomplishing clinical tasks. These protocols are established by, for example, medical societies, hospitals and healthcare providers. Some protocols are "standing" and stay in effect for the duration of care while others are specific to a circumstance. These protocols can be singularly developed or via collaborations and may be purchased or licensed with alone or accompanied by markers or other devices as part of a packaged solution. Examples of standing protocols include infection control, fall prevention, pressure ulcer prevention and rounding. Examples of protocols specific to a circumstance include changing a dressing, managing a ventilator tube, calling for back-up personnel support when it is detected that a patient's medical condition has deteriorated.

Protocols or processes of all types are comprised of tasks that have a conditional, temporal, or precedent and antecedent ordering. System 300 monitors and manages these tasks in context of the protocols that are themselves derived in context of a care plan. Monitored tasks have events and state changes that sensor and information systems are deployed in the disclosed to recognize via multimodal sensing and reasoning. System 300 enables the healthcare delivery system to transform a care plan into active monitoring and subsequent control and reporting.

The second continuous function is multi-modal sensing 310. Tasks and status are interpreted in the disclosed invention as "states" with state variables that are sensed and subsequently used to determine what actions are occurring and status is present at all times. A "state" is otherwise known as state-space in the art of control engineering. Individual attributes of the monitored people, equipment, assets change, and the state of system 300 is derived by other of the continuous functions.

As an example, a derived task or state space representation 311 is that Person B is interacting with Person A, the patient. The computer vision sensing system interprets as states that a person [derived], who is Person B [derived], standing [derived], by the bed [derived], interacting [derived] with a patient [derived], who is Person A [derived]. While the example sensing modality being described is computer vision to determine these example states of system 300, there are many sensor and reasoning subsystems that are used and viable, for example but not limited to load cells, clinical devices, telemetry, data fields from electronic medical records, microphones (sound and speech), infrared, Doppler radar, and apparatus state as communicated optically, IR, by RF(ID), or other communication means.

A third continuous function is Activity Analysis 315. Continuing the example 311, it is desirous to know the context of Person B. A visitor interacting with a patient has different state-space meaning for task and protocol management than a healthcare provider. For example, if Person B is a nurse who has traveled to a room per a schedule or a workflow request or by a discrete decision, then we infer that "Person B is performing a round and is interacting with the patient." Also in that room is the patient, Person B, and a temporal state that may be of interest is sleep, such as "The patient is calm and has been at rest for 2 hours." The activity over time is of interest.

A fourth continuous function is Protocol Anomaly Detection 320. The care plan-protocol-task-desired state logical sequence is compared to the actual state of system 300 to determine anomalous tasks or events. As an illustrative example, the desired state of system 300 is that no persons with hands not in a disinfected state should touch a particular patient who has a standing hand hygiene protocol in effect as a component of their care plan. An anomaly would be that a person who was sensed as not washing their hands is adjacent to the bed where it is known that the patient is located in. An anomaly message would be "Person B is near the bed in room 106B and did not wash their hands." Other components of system 300 will convert this message into a real time alert, a record for subsequent event or pattern analysis, or invocation of a change to one or more staff's workflow.

A fifth continuous function is Feedback For Behavior Change 325. Ultimately it is desirable that no process defects or anomalies occur because the persons or apparatus engaged are executing tasks per protocol. Knowledge of what is desired and a choice to do what is desired is used to determine the existence of process defects or anomalies.

System 300 may be utilized in several modes. As a training system, it enables a person desirous of building skills in an art to perform and receive feedback. As a warning or defect reduction embedded into the environment the process is occurring within, the disclosed converts "what is happening" to a reference and provides real time feedback before a defect happens (such as preventing a patient falling out of the bed) or as a defect happens so that it can be corrected. As an in-situ quality enhancement or training modality, system 300 facilitates the collection of facts that enables post-processing pattern discovery.

As a protocol development means, it makes tasks, their order, and their performance explicit thus enabling a more precise determination as to which comparatively more effective task sequence may result in more compliance, better process output, and better desired results. Thus, when system 300 is configured to monitor, system 300 is capable of discovering these comparatively more effective task sequences (as in to not intervene in the monitored process) and can also validate a protocol's performance. Summary reporting is enabled by the recording of observations and reasoned outputs such as state of system 300 or its compliance to desired state. The data infrastructure may be a medical event reporting system in a preferred embodiment.

As an in-situ example, an otherwise diligent care provider may have a certain pattern that would be desirous to improve if only they knew it existed: "Person B did not wash hands upon entrance to room X and at the bedside of Patient A 75% of the time between 10 AM and 12." Further supporting facts may help the discovery of process re-engineering opportunities or protocol re-engineering to increase robustness. As another example, it may be the case that patients individually have morning medications scheduled for the same time period, thus making it possible to deliver them only if the nurse rapidly moves room to room without stopping to hand sanitize. Or that the pattern occurs more often when there are five or more patients or a number of visitors or doctors present.

A sixth continuous function of system 300 is Prioritized Workflow 330. As the process of care is conducted over time, there are changes in state of the patient, other patients, the care provider, and the hospital operations itself that may necessitate proactive response(s) in order to attain the desired state, task status, protocol progress, care plan, hospital throughput, or other system level objective. As a continuation of the illustrative example, suppose that in the care plan, the admitting process made a determination that the subject patient was a fall risk. A Fall Prevention protocol is invoked and managed by a series of prescribed tasks comprising said protocol, examples being placement of a tray stand adjacent to the patient with phone within arm's length, the bed lowered below a certain height, toileting between a certain time period, bed rails raised, nurse call, TV control, and room controls placed within easy reach of the patient. System 300 uses the arts of computer vision to determine the object locations and heights while inputs might also be consumed from the bed management system should one exist as well as other inputs such as those from other state space conclusions of the system, such as that the patient has toileted. A certain time elapses and system 300 observes movements indicative of patient movement towards the rails and sufficient momentum to overcome their constraint. This anomalous state of the fall prevention protocol triggers a priority workflow message for a specific nurse or other specified or contextually determined person to respond. Such a message would take the form of "Person B must go to room X now; the patient is about to attempt to climb over rails." There is possible any combination of logic for prioritization including ascertaining the real time state space of all other patients so that the contextually appropriate workflow change is instantiated.

The computing infrastructure that persists the six continuous functions facilitates scale and leverage of the monitored objects and protocol state space such that meaning can build as was illustrated in system 300.

From a protocol monitoring system design and architecture perspective, system 300 overcomes several challenges. First, system components may develop independently, by various organizations, on various platforms, and in various computer code languages. Due to hardware and processing constraints, components are distributed over a network and therefore do not have the luxury of shared memory spaces. Also, the system's components communicate asynchronously. Each component cannot wait for other components to complete an action before continuing its own processing. Communication amongst components occurs in near real time. The loss of seconds due to communication or processing latency could result in a failure to notify agents of a potential adverse event, for example.

Also, system 300 is capable of supporting various scales, from a single space, to multiple independent spaces and from one activity in one protocol to hundreds of protocols occurring over many days, months or years. Further, the system is capable of supporting the addition of new components (e.g., sensors, reasoners, etc.) without disruption to existing system components.

The system's computerized code, memory, data storage and sundry reasoning engines may persist in one or several computers, in a dedicated or virtually scaled on demand embodiment and be located local and/or remote. System 300 is thus extensible and scalable, and has components are loosely coupled, distributed, and communicate asynchronously and in near real-time.

In one embodiment, the architecture of system 300 uses messaging, through publish-subscribe channels, as the key mechanism for inter-component communication. Messaging technology provides high-speed, asynchronous, component-to-component communication through the exchange of packets of data called messages. Message channels, such as a queue or topic, are pathways that connect components and convey messages. A channel behaves as a shared data structure between components that resides externally to the computing environment of each component. A message producer sends a message by writing to a channel. A message consumer receives messages by reading them from a channel. Each signal has its own unique message frequency.

A key advantage of messaging, and publish-subscribe messaging in particular, is it provides loose coupling between components. A publish-subscribe communication scheme allows a message consumer (subscriber) to express their interest in an event. Subscribers are notified of events when a message producer (publisher) writes a message to a topic of interest. Components can evolve independently of one another. Publish-subscribe messaging thus provides three levels of component decoupling: space, time, and synchronization. Components communicating within the scheme do not need to be aware of one another. Integration and communication happens solely through an intermediary (e.g., a message broker). Subscribers do not need to know the source of messages they receive nor do publishers need to know the destination of messages they send. Components also do not need to be actively participating in the communication at the same time. Subscribers may receive messages when a publisher is disconnected from the network. Likewise, publishers may publish messages when subscribers are disconnected from the network. Components interacting within a publish-subscribe system also do not need to be synchronized. Example embodiment schemes (e.g., subject-based vs. content-based) and topologies (e.g., star, hierarchical) are applied in message-based system 300 to cope with various scalability and subscription management requirements specific to an application.

One form of publish-subscribe communication is Message Oriented Middleware (MOM) offerings. MOM's provide mechanisms for managing messaging channels, associated message reading and writing, and also provide mechanisms for failover, security, etc. System 300 utilizes these messaging arts in a unique way to enable the continuous functions of the system to communicate, as described with respect to FIG. 4.

The high level message brokering design of system 300 is depicted in FIG. 4, according to an embodiment of the invention. System 300 is designed to consume a multitude of input signals into any number of protocol, task, or state space reasoning engines. The output of reasoning engines can inform any number of process optimization, policy enforcement, data collection, or other functions. The computerized code logic and monitored processes can be local or distributed and can work singularly, corporately, and globally.

Components can publish information to the system and subscribe to information generated by other components. Sensor-based systems such as optically based sensors (computer vision 405), as well as legacy information systems 410, publish atomic observations of activity within the monitored room via various messages. Messages are published to various topics hosted by the centralized Message Brokering System 415. Concurrently, system subscribers, such as finite state machines or reasoners 420, are given messages of interest as they are published to topics, process the messages, and may publish higher-level information back to the system (such as alerts). Additional components subscribe to alerts, process them, and disseminate feedback as appropriate (e.g., via email 425, audible alerts 430, etc.). Because each finite state machine corresponds to a unique protocol, the system can be expanded or reduced in size based on the number of protocols being monitored. Further, the system is very scalable, and can be on a patient level, room level, department level, or hospital level, as examples.

In one example embodiment, each message exchanged within the system is a well-formed XML (eXtensible Markup Language) document defined by an XML schema. An XML schema defines the structure of an xml document, its fields, valid values and ranges for fields. The XML schema is shared by system components and provides an enforcement mechanism to ensure communication is consistent across the system.

Figure 5:
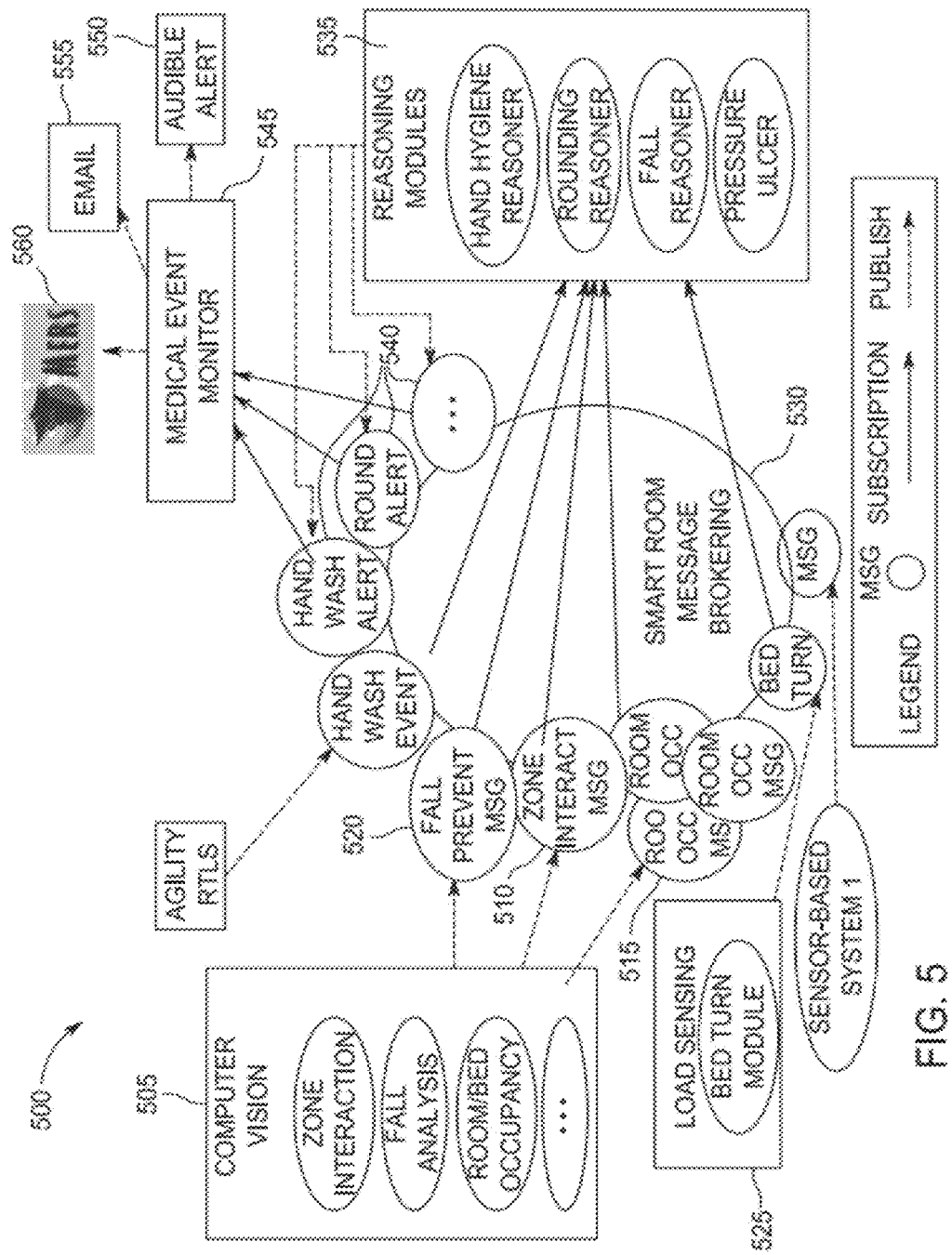
FIG. 5 is a schematic of a message brokering system, in accordance with an embodiment of the invention.

FIG. 5 is a schematic of an exemplary message brokering system for a Smart Hospital Room for Patient Safety, in accordance with an embodiment of the invention. The Smart Hospital Room for Patient Safety focuses on the monitoring of activity within a hospital room and ensures various clinical protocols (e.g., hand hygiene) are being followed. As one example embodiment, the geospatial zones of a hospital room are established as having clinical process context. Objects and motions in these zones have protocol meaning that task reasoning engines track over time. The flow of information to and from these components is handled by a message brokering system. This architecture allows the system to be scaled as desired to monitor any number of processes and events, locally or globally.

In the example illustrated in FIG. 5, a Computer Vision Component 505 continually monitors a hospital room and publishes observations to the Smart Room Message Brokering System 530 including the position of caregivers in the room (with respect to predefined zones) 510, room occupancy 515, and the position of a patient with respect to the patient bed 520. Pressure sensors, embedded in the patient bed, communicate with a Load Sensing module 525 that publishes observations regarding the position of the patient in the bed to the centralized system. Each observation is published as an XML message to a different topic that is managed by the system's message broker 530. A Hand Hygiene Reasoner 535 listens for zone interaction messages 510 and reasons over the order of movements of caregivers within the room. In the example protocol logic, if a caregiver enters the patient zone before entering the hand wash zone, the protocol has been violated and alerts are published to an alert topic. The Medical Event Monitor 545 subscribes to protocol violation alerts and, depending on the severity of the violation, provides feedback in near real time. This feedback may be audible 550, visual, or text-based (e.g., email 555). The intensity of feedback may be varied depending on the severity or type of protocol violation. Feedback may be provided in real time or post event. Feedback may also be integrated into process quality systems (such as Medical Error Reporting System 560).

Figure 6:
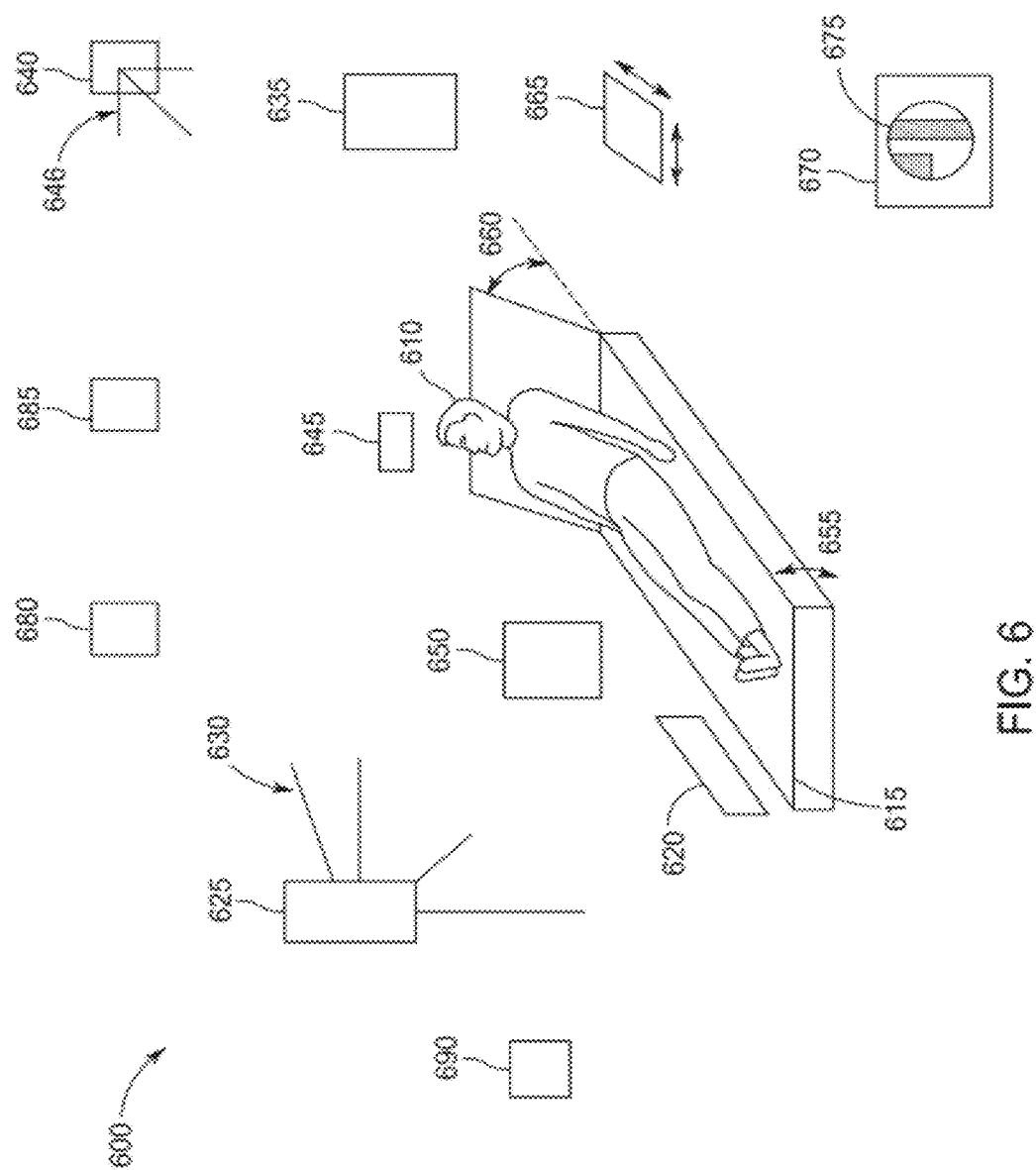
FIG. 6 is a schematic of a room configured for clinical event detection, in accordance with an embodiment of the invention.

FIG. 6 is a schematic of a room 600 configured for clinical event detection, in accordance with an embodiment of the invention. Objects in rooms and their placement are typically desired to be within prescribed heights, locations, and distances for various protocols. Examples include bed configuration, reach of trays, phones, and orientation of tubes and people. Line of sight for optical sensing must be established as appropriate. Accordingly, a number of sensing modalities may be used to detect system states and potential breaches in protocol and their associated confidence/ambiguity measures. As described in detail below, such sensing modalities may include networks of cameras and 3D range imagers used for computer vision analysis; RFID, optical or IR tags which allow for the establishment of identity and proximity; low cost sensors such as motion detectors and load sensors; and/or optical tags for object and person recognition, according to various embodiments.

Using the example embodiment of a hospital room 600 configured for clinical event detection, a patient 610 is located on bed 615 within the field of view 630 of a camera 625, which may be configured as an optical sensor according to one embodiment. Room 600 may include any number of cameras or optical sensors according to various embodiments. Within the field of view 630 are a number of devices 650, 645, 635, and 680, associated with the protocols of care for patient 610. Devices may include, for example, clinical systems such as a ventilator or O2 device 650, telemetry apparatus and connections to fixed systems such as oxygen supply or telemetry networks 645, intravenous poles with dispensers 635, hand wash or sanitizer station 680, and human interfaces such as computer screens, lights and sundry markings.

Bed 615 has attributes that are also monitored and within field of view 630. These include the orientation of patient 610, angle 660 of bed 615, height 655 of bed 615, and the location of its bed rails 620. Miscellaneous items such as the phone and bed pans may be located on stationary or moveable tables 665 and these too are within field view 630 of one or more sensor(s) 625.

A plurality of optical sensors 625 may be employed to establish singular or multiple views. Computer logic may utilize single or multiple sensors together in the process of calculating the state space of activity, patient or apparatus.

The invention has the ability to consume optical patterns or IR that are generated on devices such as indicators or wave forms as well as those of tags. These are to be placed in the field of view 630 for the purposes of item identification and marking for a clinical event or optically communicating the state of the device 670 being monitored. Devices, components, and disposable apparatus, such as, tubes, dressings, catheters, phones, tables 665, clinical systems 650, bed rails, 620, and etc. may have labels 675.

Devices and apparatus such as clinical systems 650 and drug dispensing devices 635 may have visual and audible outputs that may also be monitored by the disclosed system. An experienced care provider is attuned to time series or state data such as an EKG pattern, the sound of a ventilator alarms and the level in an intravenous bag as well as the associated clinical context. In a similar way, the disclosed invention's intent is to monitor clinical care, reason what is happening, the state space, and provide the appropriate care provider logical clinical workflow and decision support assistance in near real time as well as information for post process analysis.

To achieve this beneficial functionality, visual and audible inputs may be gathered. Sound capture device 685 such as a microphone may be deployed in one or several locations and may be unidirectionally aimed or broadly acquisitional. Monitored sound may be from devices or people such as the patient 610 or others such as care providers, staff, or guests. The sound frequency may be any desired. The sounds are interpreted by voice and pattern recognition algorithms that are prior art.

Devices and activities producing monitored visual and audible signals may be designed to produce such signals in a way that their optically or sound outputs are more easily captured by optical sensors 625, field of view 630, and or via sound acquisition 685. The ranges of said outputs can be outside of the human detection ranges, such as, near IR or above 20 kHz.

One or more range devices 640, such as, for example, range radar, Doppler, or LIDAR, may also be deployed with its distance detecting vectors 646 positioned such that data associated with monitored clinical events, bed 615, patient 610, apparatus 635, 650, 665 may be acquired.

Consumable devices 670, such as dressings, drapes, and tubes associated with ventilators, wound drains, central lines, IVs, and catheters may be used in conjunction with the protocols that comprise a patient's care plan. Devices 670 may be tagged with patterns 675 that optical sensor 625 can detect. Patterns 675 may be specifically designed for use with system 300 or may be bar coded using uniform industry standards. Devices 670 may also be tagged with passive or active RFID and/or IR pulse. System 300 consumes tag information using the reasoning and workflow logic described herein.

RFID-based tagging and location services may also be incorporated within room 600. RFID detection 680 is utilized to monitor clinical events such as a tube use and personnel identification using sensors enabled with RF output. RFID detection is used in conjunction with the protocols being monitored as part of the clinical workflow. Additionally, RFID, IR, optical, and other sensors may further be utilized to train the computer vision recognition algorithms or check its precision.

An example of RFID incorporation is in a fall prevention protocol called by the clinical workflow. In the example protocol, a number of events are included as tasks for nurses and care technicians to execute. A patient interaction before 9 PM and after 7 PM by the nurse is an example. Upon entering the room, an RFID enabled tag being worn by a person is detected as that of the nurse. Time is 8 PM, which is within specification. The phone on movable stand 665 is to be within reach of patient 610. Optical sensor 625 senses that the phone, tagged 675 is on table 665 and within a specified set point distance of bed 615 and patient 610. Bed rails 620 are up, height 655 and angle 660 of bed 615 are detected by one or both optical sensing 625 and range radar 640 or dedicated sensor device such as that available from a bed so equipped. The care provider is detected as being at bed 615. Further, microphone 760 gathered audible words, interpreted by reasoning engine 750 as patient 610 being asked if toileting is desired and a negative response recorded. In this present example, the fall prevention protocol's clinical activities were followed, during the appropriate time.

Figure 7:
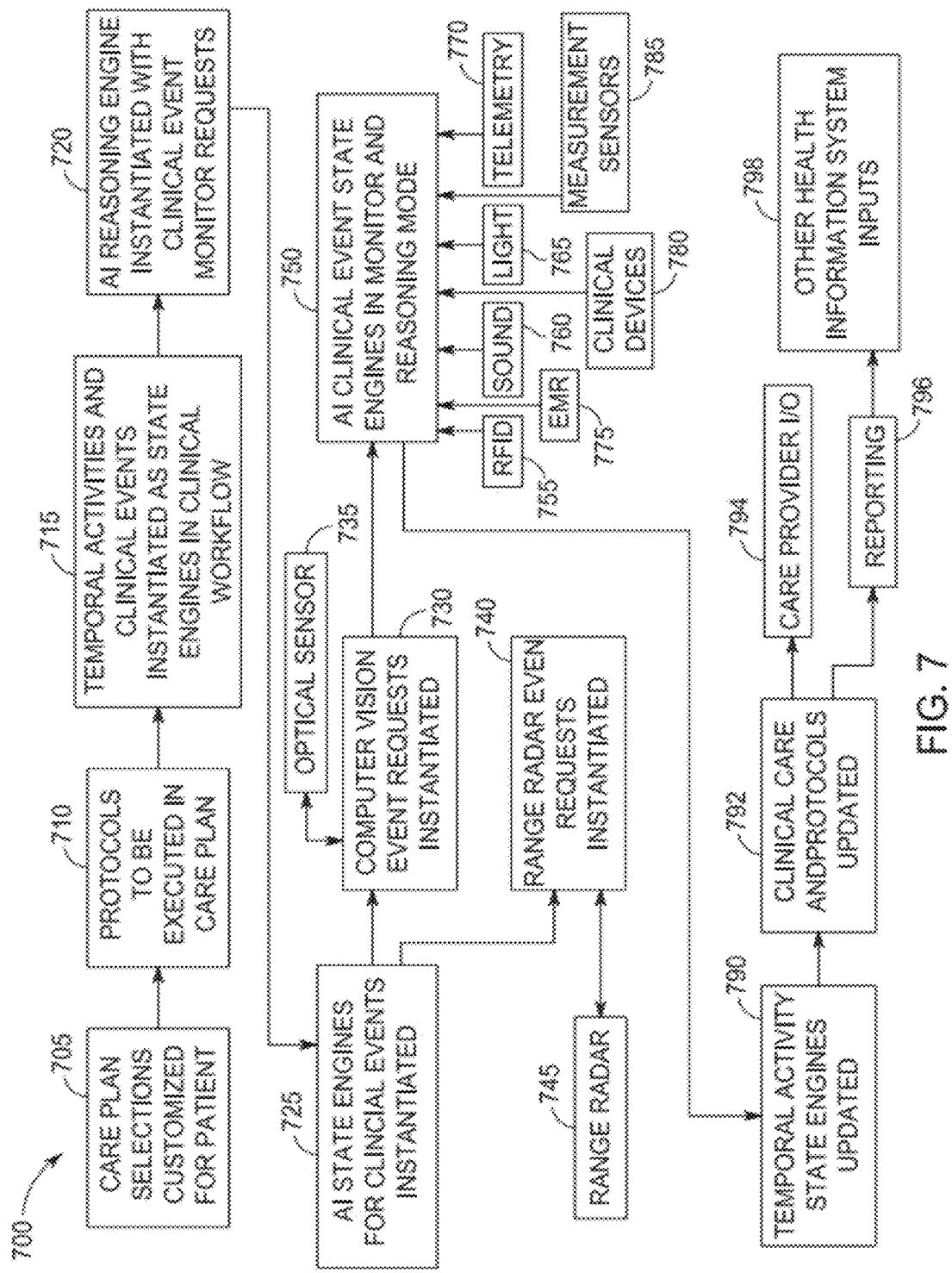
FIG. 7 is a block diagram of a closed loop protocol monitoring system according to an embodiment of the invention.

FIG. 7 is a block diagram of an analytical system 700 that enables closed loop protocol monitoring, according to an embodiment of the invention. System 700 converts desired protocols into tasks that are subsequently monitored, contextually reasoned over, and output for feedback, reporting, and workflow interventions. The subsystems are connected via a message brokering system (FIGS. 4 and 5). System blocks may be instantiated locally or remotely, according to various embodiments.

Decision support engines and analytical workflow proceed through a sequence where in a patient's care plan is converted into requisite protocols and clinical tasks. These protocols and tasks are further configured into workflows with tasks that are to occur within a desired sequence and time or in response to medical reasons. It is the active configuration, monitoring, interactivity with and event logging with summary reporting that the system disclosed herein beneficially enables and aids. Ultimately, care and the judgment required to provide it well resides with skilled healthcare providers. As such, the disclosed system's intent is to back these skilled professionals up with sophisticated decision support and high integrity data to use for pattern discovery, effectiveness, and skill building.

The admitting team or care providers assess a given patient's medical condition. Suitable treatment plans for that patient are selected. Within a care plan are one or more protocols. A protocol, treatment plan, or desired care plan 705 for a patient has one or more tasks. There may be hundreds of protocols required with conditional branching depending upon the patient's medical or physiological state. Examples include standing policy as well as particular operating procedures and protocols uniquely specific to a patient.

Protocols to be executed in a care plan 710 are selected based upon care plans for a given institution. These are configurable by institution and are the codification of its care policies. Further, care plans, protocols, devices, and apparatus packaged by other entities may also used in conjunction with system 700. The institution specifies a standard set of protocols 710 for types of care provided. These protocols may be, for example, designed to incorporate clinical event markers that the present system selects as part of the protocols 715. Unique protocols to be executed and followed may also be selected beyond those which are the standard of care said institution specifies. For example, an institution my compare its processes of care to other institutions for an assessment of the most comparatively effective methods of care. System 700 beneficially enables a design of experiment to facilitate the determination of comparatively more effective care and apparatus used in care in conjunction with the fact base of exactly what the patient and activity state space was determined as and when, within and across institutions.

To monitor activity, events and manage workflow, the processes of care are designed purposefully. An example embodiment, such as hand washing, is used to illustrate an enabled process of care. In the prior art, a protocol such as hand washing, disinfection or sterilization for patient care may be a standing element of a care plan. Staff are instructed to wash or hand sanitize prior to delivering care. Yet, via anecdotal evidence and via audits, it is known that providers of care do not always execute this clinical event. In some cases, a medical emergency leads to actions more warranted than hand sanitation. In other instances, staff has neglected the activity. In many instances, it is not detrimental to the care of a patient that a care provider actually does not wash their hands upon entry into a patient's room as may be the policy, as in these instances no patient or sterile or disinfected surface of need or interest was contacted such as when a staff member entered, talked with the patient but never placed their hands on or near the patient or medical devices that are required to be handled with sterile procedures.

Therefore, a beneficial aspect of system 700 provides the mechanism to use more clinical content to reason if it is required to sanitize hand. Through its use of computer vision, Doppler range radar, Lidar, IR, RFID, and other sensor systems, system 700 is able to monitor, manage and report dramatically more nuanced protocol steps because it can reason what is occurring and compare monitored events to these more nuanced protocol steps. The true essential hand-washing events are differentiated from non-essential. This improved discrimination enables more staff acceptance and measures of compliance.

Purposefully designed protocols called as part of a patient's care plan 705, 710 are loaded 715 as temporal activities and clinical events and instantiated as state engines within a clinical workflow. Each protocol's sequence of tasks is monitored. The state of said tasks is tracked cohesively. According to various embodiments, the protocols are managed and prepared in a similar manner as described in US Patent Application Publication No. 2009/0119126, which is incorporated herein by reference. In one embodiment, the tasks within this collection and sequence are monitored with state reasoning engines 750. Deviations and logic impacting workflow is in active communication with other elements of the disclosed system and other hospital systems such as bed boards and electronic records.

Different protocols to be monitored and managed may use the same clinical events. For example, that a round was made or the patient toileted or that the patient had a certain pattern of activity could be used by two or more protocols. For this reason, clinical protocols and workflows are separated from clinical event detection.

Embodiments of the present invention gather requisite information and post it to the artificial intelligence (AI) reasoning engine 720. Events and tasks whose states are desirous to determine are requested by the clinical workflow 715. As previously disclosed, clinical tasks and the protocols that define them are designed to have detectable elements, such as sensor patterns, optical tags, Geo-spatial positions, temporal sequences, manual inputs, and the like.

AI engine 750 reasons over sensor system outputs to determine the state of activities or the requested clinical events posted. Any number of concurrent engines 750 may be active, each instantiated with a request sent to it by the clinical workflow 715. Inputs can be optical sensors 735 that are interpreted by computer vision 730, vector space resolved 740 from Doppler range radar 745, Lidar 745, RFID or IR 755, EMR data 775, sound resolved for voice or pattern 760, discrete, analog, or digital clinical device outputs 780, lighting level or room air condition 765, measurement sensor systems 785, and telemetry 770. One skilled in the art will appreciate that many more devices, systems and data, manual inputs, and statistical inferences can be consumed by AI engines 750 to ascertain the state of an item of interest in the clinical care pathway.

Upon executing the algorithms used for reasoning what the state of a requested item is, the temporal activity states is updated 790. An example is that a room may have a patient, but no care provider present (two states determined by two reasoning engines 750). If no care provider is present for a set period of time as specified in a rounds protocol, clinical care and protocols may be updated 792 and the nursing coordinator may, for example, desire to be notified or a reminder sent to the nurse assigned to that patient 794. A historical record is recorded 796 of the round not being performed for post processing medical event reporting and analysis. Other systems such as EMRs, medical event reporting systems, bed boards, workflow engines and the like may also receive state or clinical process information 798.

Figure 8:
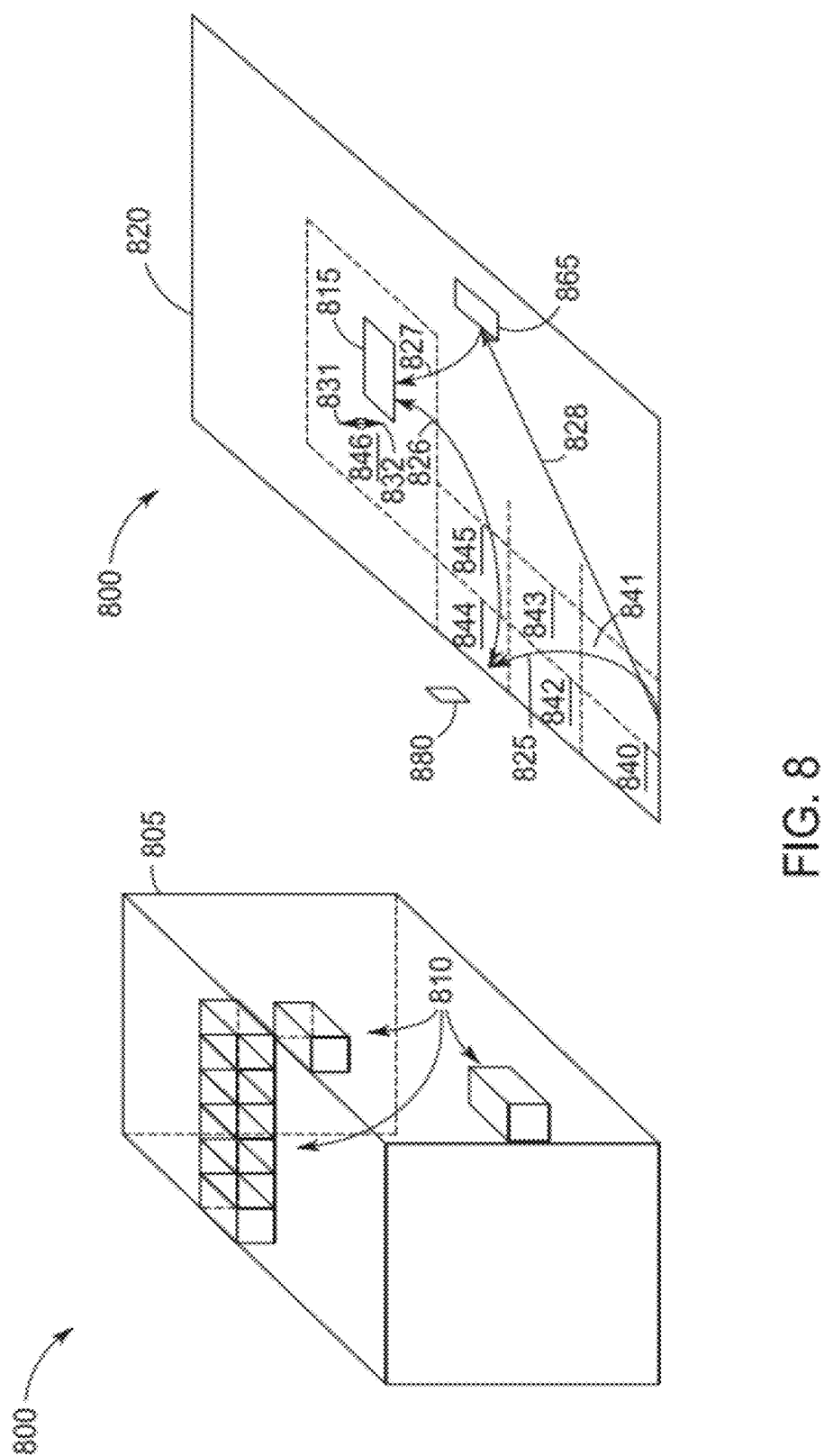
FIG. 8 illustrates a spatial-temporal arrangement for computer vision detection, in accordance with an embodiment of the invention.

A large number of protocol activity states can be reasoned using location and time. In an example embodiment of the invention, computer vision provides location information that the AI engines use for protocol activity state reasoning. Referring to FIG. 8, a spatial-temporal arrangement for computer vision detection is illustrated, in accordance with an embodiment of the invention. A space 800 such as a hospital room is monitored for the activity occurring in that space 805. Space 800 can be planar 820 or volumetric 805. Space 800 is divided into a number of subsections 810 to track movement over time and facilitate prescribed protocols.

In one embodiment, the optically monitored space 805 in which protocol tasks are performed is divided into a number of meaningful geo-spatial zones, which may comprise one or more subsections or zones 840-846. The crossing of identified objects amongst these zones has contextual meaning. Using hand washing and a planar space 820 as an example, a moving entity such as a person may be tracked using a planar zone location detection. Various items are located in space 820, including a hand wash station 880 in zone 844 and a hospital bed 815 in zone 846.

An exemplary protocol may be that upon entrance, a person must dispense hand sanitizer located in hand wash station 880 before proceeding to bed 815 of the patient. A person's entrance into the room is detected by activity in zone 841 and path 825 from the first zone 841 at the door is detected through zone 843 and zone 844 where the hand wash station is located. Dispensing of fluid may be detected from an RFID sensor located in the dispenser through the use of a vapor detection sensor to determine fluid dispersal. According to alternative embodiments, other devices such as sinks, sensors such as water flow, soap, or chemical detection may be used to track hand washing. Alternatively, dwell time in zone 844 may be used as a proxy for dispensing. Accordingly, the system is able to incorporate optical sensing, path, and protocol context.

The entering person then proceeds along path 826 from hand wash station 880 at location 844 to bed 815 in another specified zone 846. Accordingly, AI engine 750 determines that the state of the person is in room 805, sanitized hands, located at bed 815. Assuming a protocol that entering persons must sanitize their hands to be near a patient, AI engine 750 can reason that the protocol has been met. Extending the example embodiment, if the person entered the room in zone 841, followed path 828, and directly touched tray 865 that is located adjacent to bed 815, and proceeded along path 827 to bed 815, a hand wash protocol lapse is recorded.

In another example embodiment, a patient is deemed to be at risk of falling out of bed. The system is configured to monitor for predecessors of falls and to notify the shift nurse should the risk of a fall pass a certain threshold. In the example protocol, the height of bed 815 is to be lowered from elevation 831 to 832 and tray 865 is to be adjacent to bed 815. Other steps may be that the phone is to be on tray 865 and that bed rails are elevated.

Additionally, verification that a patient has toileted and rounds have been made are examples of any number of specific activities to be monitored. Alarms are appropriately sent to the personnel responsible for the protocol tasks at the appropriate time or change of state of another aspect of the patient or room, such as lights out, manual input, verbal command and etc. The risk of fall likelihood and injury may be used to calculate the priority of alarm or sensitivity of the system. The detection sensitivities in both sensors and reasoning as well as dynamically added protocol steps are adjustable and configurable based upon any agent of the system's characteristics. An example being a heavy patient's propensity to fall from a given location versus a lighter person, or an experienced care giver's response time constant versus a person with less observed or characterized capabilities.

FIGS. 9-12 illustrate exemplary ontologies for agents, objects, actions, and events, in accordance with embodiments of the invention. The reasoning engines determine the state of people or agents 900 (FIG. 9) capable of performing actions, objects 1000 (FIG. 10) that are the recipients of the actions, actions 1100 (FIG. 11) that are defined at computer vision detectable granularity, and events (FIG. 12) that include associating actions with agents and objects and tagging events with times. An ordered ontology is utilized so that protocols and their elemental state spaces can be understood across a domain of practice or application, such as healthcare. The ontology is specified for a given domain of application. In healthcare, a person's role, an object's sterile state and movements are examples. The contextual meanings may be prescribed or learned/trained.

Figure 9:
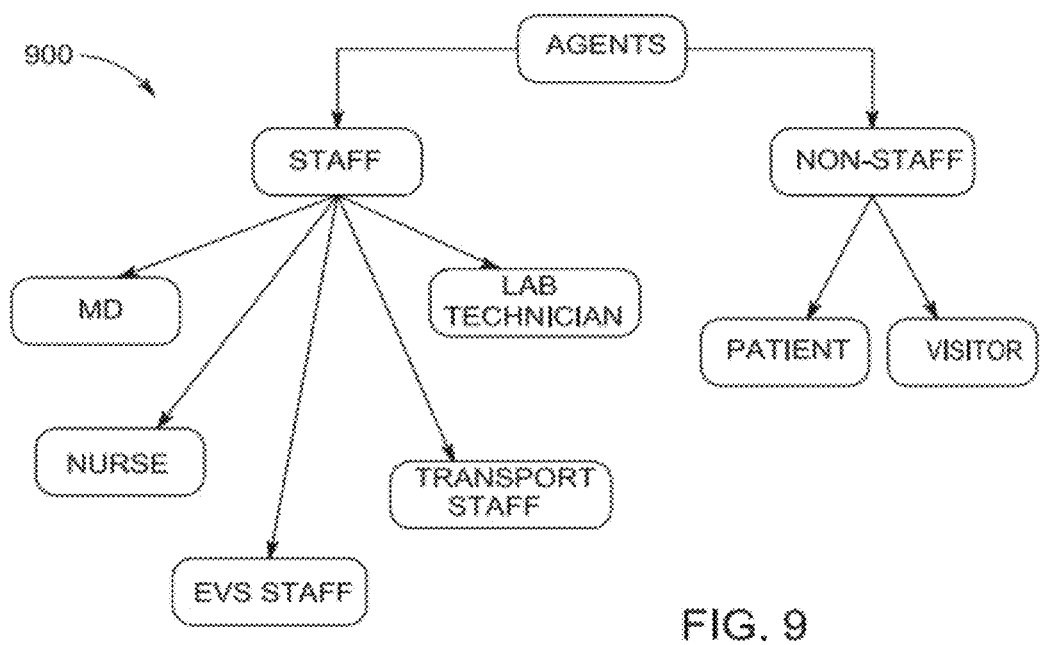
FIG. 9 is an exemplary ontology for agents, in accordance with an embodiment of the invention.

Referring first to FIG. 9, an exemplary ontology 900 is illustrated for persons being monitored in the process of care such as types of staff (each having contextual roles) and non-staff such as patients and visitors, which can have multiple specific instantiations for each domain. FIG. 9 shows this for the Healthcare domain where the Agents 905 is initially broken into two specific instances Staff 910 and Non-staff 915. The agent-category Non-Staff 915 can be further categorized as Patient 925 or a Visitor 930. Similarly the agent-category Staff 910 can further categorized in five sub-categories as indicated by 920, 945, 935, 950, and 940. These well-defined roles have specific attributes used by the reasoning engine's logic. For example, knowledge of a person's role may allow for an inference such as: "A nurse is a medical practitioner."

Figure 10:
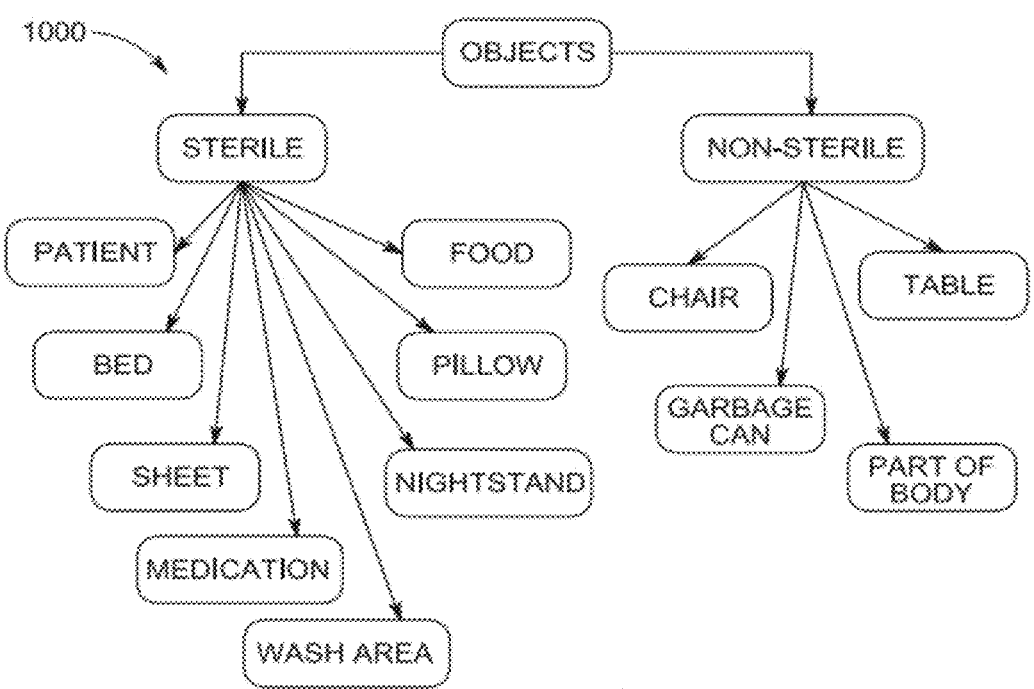
FIG. 10 is an exemplary ontology for objects, in accordance with an embodiment of the invention.

Referring now to FIG. 10, an exemplary ontology 1000 is illustrated for objects being classified as in sterile or clean states. As in FIG. 9, well-defined meaning for monitored elements in the care delivery system is used in order to reason in an automated way. Objects can be many and each may have various states. Further, what objects are in these states is well or robustly described. An alternate approach to protocol reasoning is an ontology engine that uses sensor information from the clinical environment to update the properties of the ontological objects which are used to infer protocol violations. For example, the caregiver object of the ontology has the following three properties: hygiene_status which can take values from {clean, unclean, unknown}, positionType which can take values from {atBed, atWash, atDoor, inRoom, outRoom} and positionId which can take the value of any string literal. Based on sensor input to the ontological engine, the ontonology engine uses Horn clauses to infer change in object properties. These properties are designed so as to be relevant to the various protocols being monitored. Protocol violations are inferred based on rules related to object properties and their spatio-temporal relationships with other object properties. For example, assume that a caregiver has hygiene_status property as "unclean". Assume further that based on the information from a sensor, the caregiver's position property changes to atBed and positionID='2'. If the "bed" object with ID='2' has the object property is Occupied=true, then a handwashing protocol violation is detected.

Figure 11:
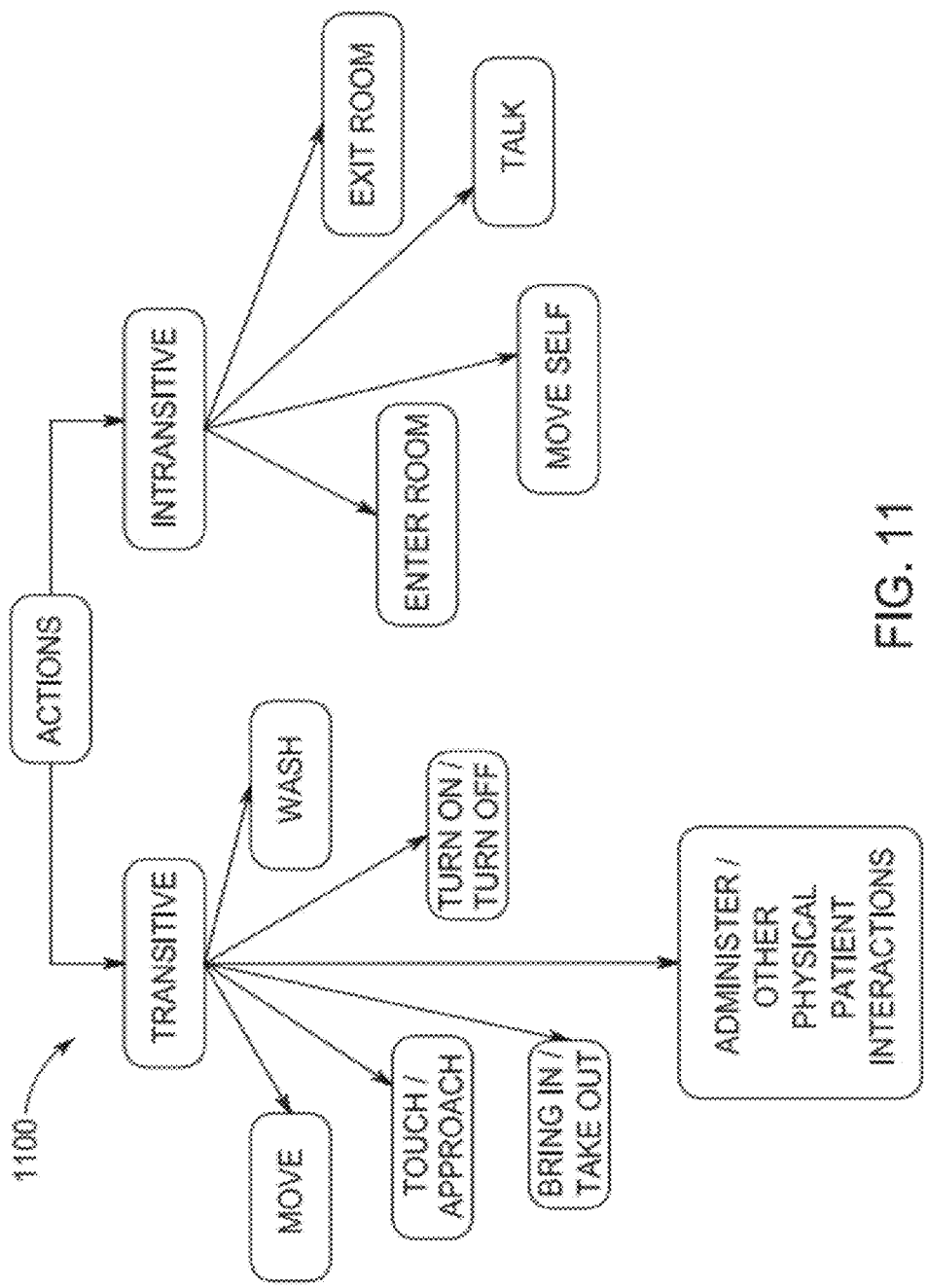
FIG. 11 is an exemplary ontology for actions, in accordance with an embodiment of the invention.

FIG. 11 illustrates an exemplary state space 1100 for the actions of monitored things. As in FIG. 9, the action state of persons and objects is required for protocol monitoring and decision support. The transitive action of an object or person may be dependent upon a specific monitored and specifically identified object or agent, through time. Alternatively, action may intransitively be classified—such as for an as yet unidentified specific object or agent. The states "transitive" and "intransitive" may toggle for objects or agents, though the preferred state is one that transitions to and stays transitive so that there is a directly tracked activity within monitored protocols.

Figure 12:
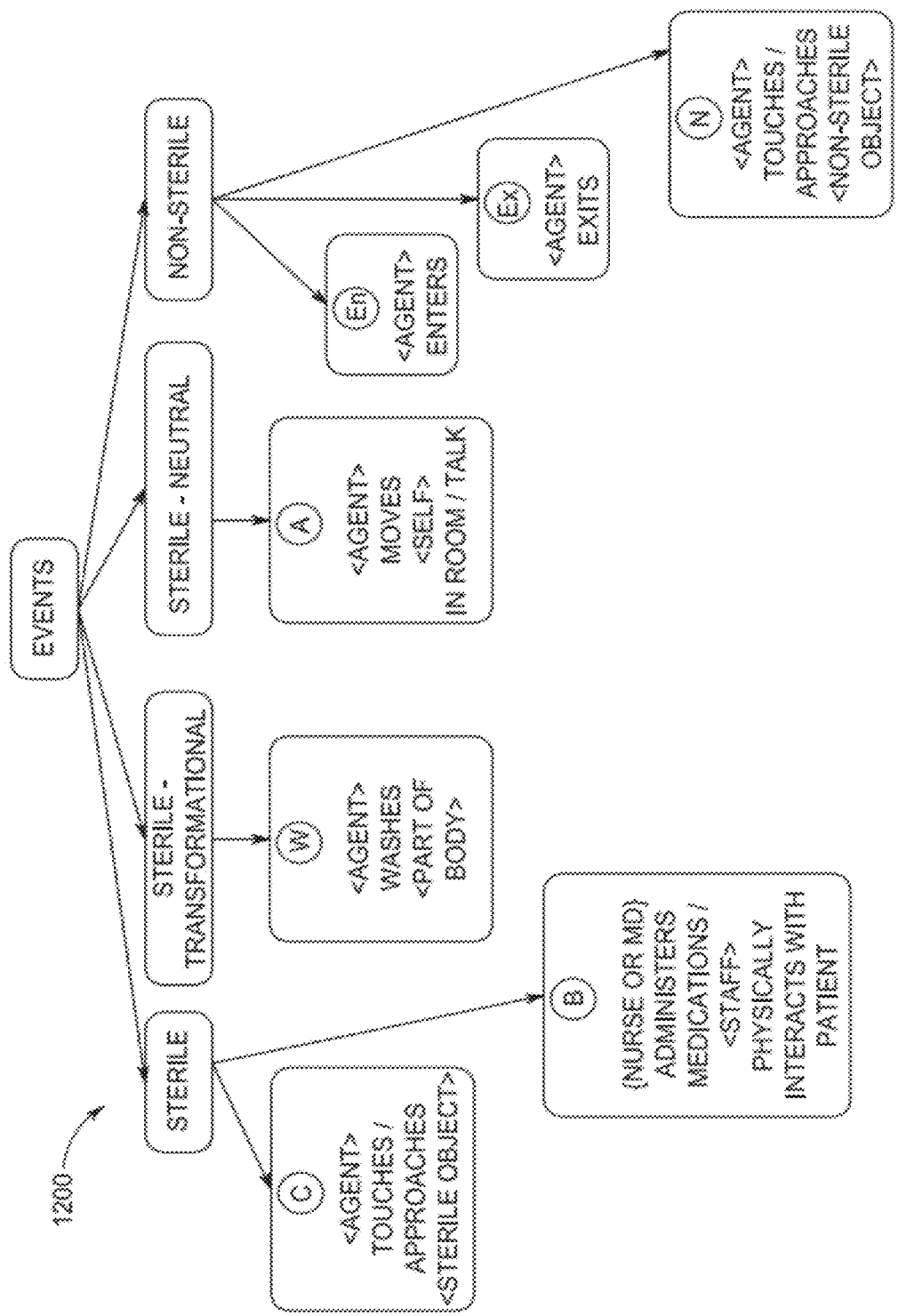
FIG. 12 is an exemplary ontology for events, in accordance with an embodiment of the invention.

Referring now to FIG. 12, an exemplary state space 1200 for events is displayed where a well-formed definition of the state of a monitored object or agent is made. As in FIG. 9, the robust categorization of monitored protocols and environments is desirable. By assigning a differentiated "word" such as "A," "B," "C," "N," "W," "En," and "Ex" to events, there is explicit meaning assigned to the state of the observed. That meaning can then be reasoned over mathematically, as illustrated in FIG. 13.

The AI engine consumes meta-data descriptors produced by the various sensing modalities and determines whether or not a breach in protocol has taken place. Within this contextual clinical world, the AI engine uses a Markovian representation to model and reason over the clinical environment. Referring now to FIG. 13, an exemplary augmented transition network (ATN) is illustrated for correct and incorrect state transitions, in accordance with an embodiment of the invention. The progression of states of objects, people, and movements is used to determine if the activities or states of objects or people are consistent with the desired progression prescribed by a protocol. Violations of protocol can result in process defects such as an unsterile hand touching a sterile wound or dressing, thus increasing the chances for infection. An example of a protocol may be that before touching a patient, the entering person must wash or disinfect their hands and do so again upon exit if they did touch a non-disinfected surface but not required to wash if non-contaminated surfaces were not touched. Gloves or other infection control means may also be monitored in temporal sequence context, an example being that hand disinfection first, then glove, then patient, then glove removal, then hand disinfection, and so forth. Similar sequences may be used for gowns, drapes, and other components of infection control protocols.

Figure 13:
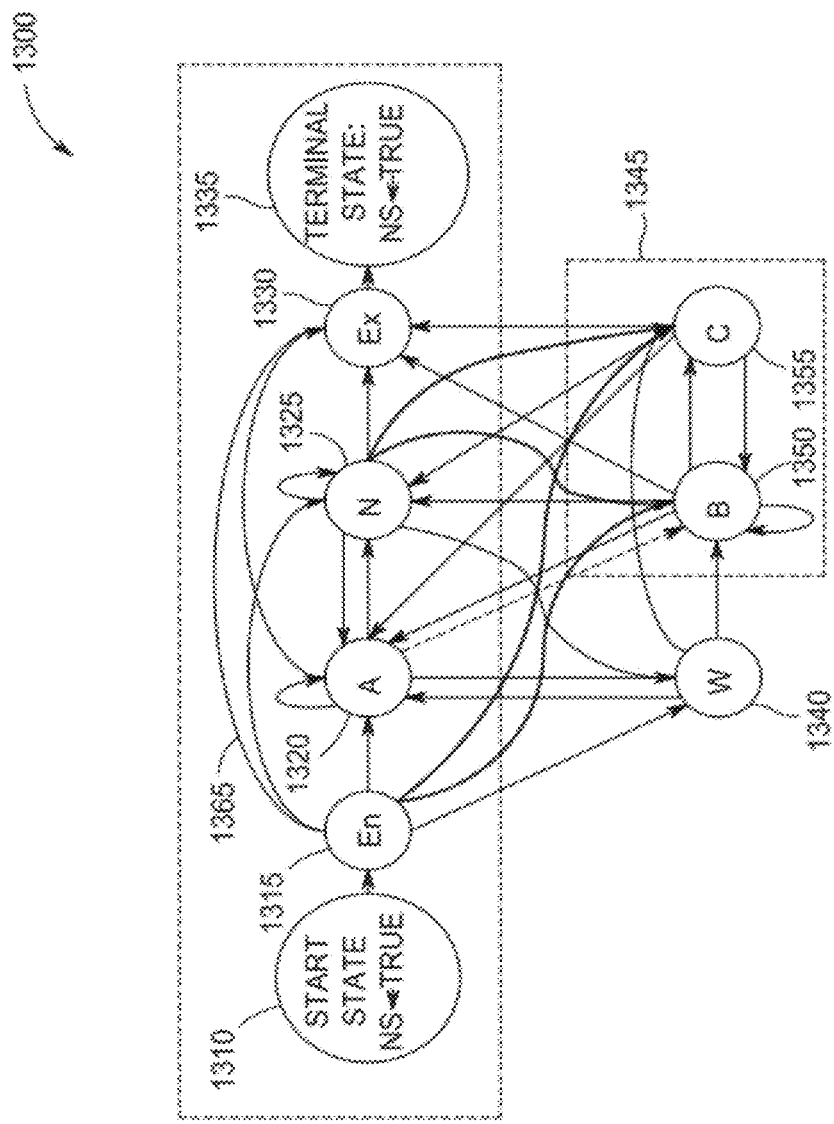
FIG. 13 is an exemplary augmented transition network, in accordance with an embodiment of the invention.

As illustrated in FIG. 13, a valid protocol is modeled using a state transition network 1300, in which each node 1310 is either a "start" state 1310, an "intermediate" state 1315, 1320, 1325, 1330, and 1340, or a "terminal state" 1350, 1355. Example states could capture information such as "Person A, who is a nurse and thus a medical practitioner, has just touched Person B who is a patient and is about to leave the room." Transitions 1365 can take place between any two nodes (including themselves). Transitions 1365 exhaustively capture all possible states that are relevant to inferring breach of protocol. Any of those states that lead to breach of a defined protocol 1350, 1355 are thus encoded in the network and when there is a breach, the network is able to create an alert.

The AI engine is robust to noisy or missing signal inputs. The reasoning mathematics identifies that a signal quality has changed and will be dynamically adapted to the quality. Output state space confidence will be dynamically adjusted.

The granularity of state information within which the AI engine reasons is a function of what is sensed by the various sensing modalities. For example, one instance involves a set of sensors in the room that are designed to identify specific pre-defined zones in the clinical room. In this example, the system is designed to robustly infer states described in terms of presence or absence of people in the pre-defined zones, such as subsections or zones 840-845 discussed with respect to FIG. 8. The corresponding state transition network would now reason with states in terms of people entering and leaving the predefined zones in the room to infer breach of protocol. Another instance could be RFID-based sensing modalities that can signal the identity as well as location of people in the clinical room. In this case, the states visible to the reasoning engine include information about exact location of a person and their clinical role.

Multiple protocols can be applicable for a given clinical environment based on medical knowledge related to the patient as well as requirements and constraints imposed by medical knowledge. Individual protocols are encoded as separate state transition networks. A protocol can be patient-centric, practitioner-centric, bed-centric or room-centric, among other possibilities. And since a single room could have multiple patients, practitioners or beds, the AI engine instantiates one network per such instance for as long as there is potential for the corresponding protocol to be violated. Hence, an ensemble of state transition networks may be active for a given room, that are dynamically created or destroyed based on whether they are required. For instance, when a practitioner enters the clinical room for the first time, the AI engine might trigger a state transition network for monitoring if that particular practitioner is compliant for hand-hygiene protocol. The network is active as long as the practitioner is in the environment, but when the monitoring system signals that the practitioner has left the room, the AI engine destroys the network instance since protocols related to that practitioner are no longer required to be monitored in the context of that clinical room. If however, a monitored person's context is clinically or process relevant as their path or activity extends past the room, such as in a hallway, the network remains active, consuming optical as well as other sensor system inputs as available, such as, for example real time location services such as RFID.

Another feature of the AI engine is that it is agnostic of the geometry of the clinical room being monitored. The information consumed by the AI engine contains no knowledge specific to the geometry of the room. This is consistent with the fact that protocol definitions are largely independent of the room geometry as well. This feature enables the AI engine to be equally and easily extensible to multiple room configurations without requiring redesign.

Protocols can define illegal state transitions using the following types of constraints: absolute spatiotemporal property of a state, for example the time of the day in which it occurs or the location in the environment in which it occurs; relative spatiotemporal conditions that have to be met at a given state or node, for example maximum time allowed at a given location or the smallest distance from a given point in the environment; spatiotemporal relationships that have to be satisfied between pairs of states, for example state s1 cannot occur before state s2; and knowledge-rich or medical conditions that have to be met as preconditions, as examples.

In order to instantiate such a node transition network the AI engine uses a variation of augmented transition networks (ATN) 1300 as illustrated in FIG. 13. ATNs not only allow for the description of state transitions but also provide means to specify as well as modify information associated with each node, the ability to reason across disconnected network components, and the means to modify and transfer information across the network.

Figure 14:
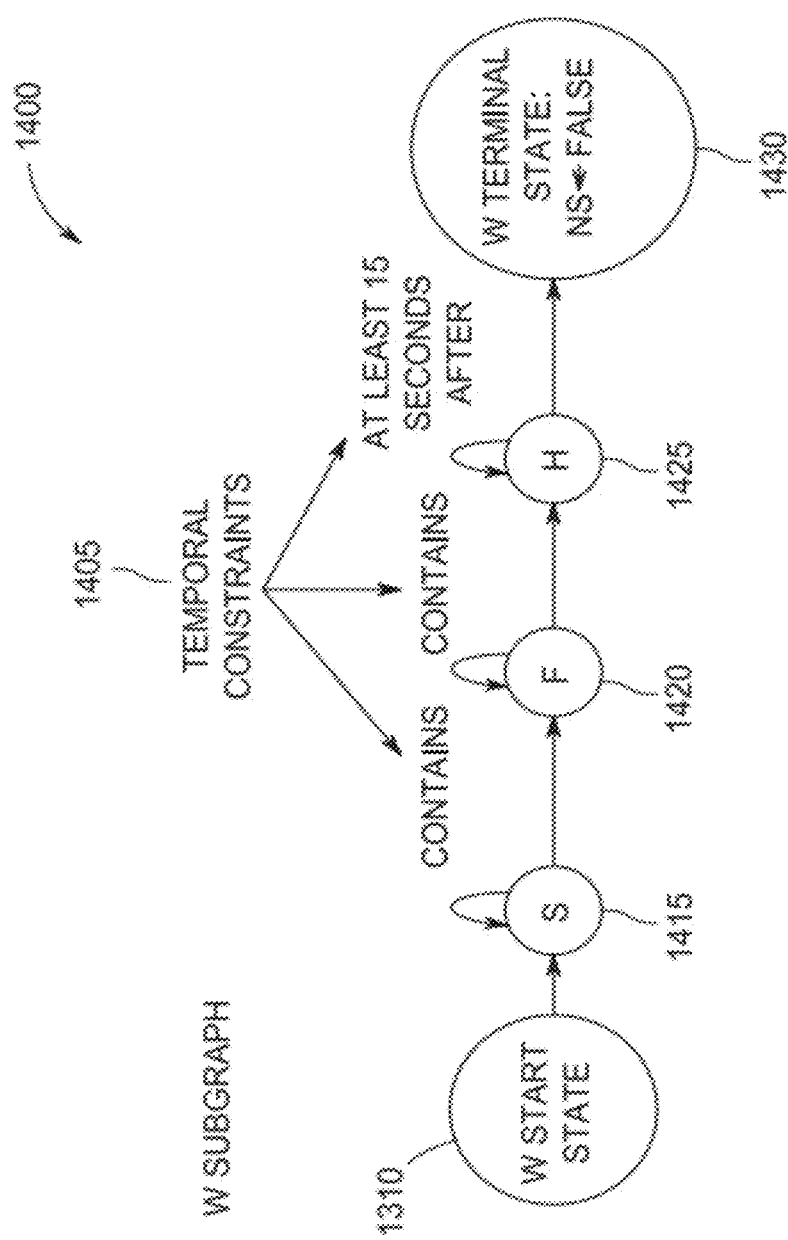
FIG. 14 is an exemplary sub-graph corresponding to a node of the augmented transition network of FIG. 13.

For example, node W 1340 in the ATN 1300 involves a branching to a subgraph 1400 as illustrated in FIG. 14, which has independent state logic, represented to reason about node W 1340 in FIG. 13. The sub graph 1400 returns back to node W 1340 in FIG. 13 after it completes its reasoning with state information 1430 in FIG. 14 that will be used by the logic in the main ATN 1300 to move from node W 1340. The ATN will be used to represent the problem as a non-deterministic transition graph, where a node can have transitions to many other nodes. In FIG. 14, node W is used as an example process step, which is hand washing as a task in the hand washing protocol being monitored in the example embodiment. It is often desirous that a temporal aspect to a task is considered, such as, for example how long a person washes their hands or a sequence of certain activities over time.

Many aspects of reasoning about protocols use temporal reasoning or reasoning with time-instants and time-intervals. The AI engine is complemented by Tachyon, a general-purpose constraint-based system for temporal reasoning. Tachyon provides a powerful and flexible model of events and inter-event constraints. It is capable of reasoning about both qualitative and quantitative aspects of time, by allowing the user to represent parameterized temporal constraints over states and state transitions. All temporal relationships (i.e., before, meets, overlaps, finished by, contains, starts, equals, started by, during, finishes, overlapped by, met by, after) can be represented in Tachyon with interval valued constraints (e.g., at least 15 seconds and at most 2 minutes after). Tachyon solves these constraints using both optimal and heuristic solution techniques. According to one embodiment, Tachyon is used to convert raw computer vision outputs into state representations for use by the ATN.

In the examples of patient safety protocols used as example embodiments here in, such as hand hygiene, rounding, patient fall prevention, pressure ulcer prevention, and ventilator-associated pneumonia prevention, etc., use a sensing and processing system that is capable of determining the location state such as when a caregiver enters/leaves the room, where the caregiver stands at any point in time, does the caregiver approach the hand hygiene dispenser and press it, does the caregiver touch/interact with the patient, when the patient makes a turn (either by himself/herself or with help from the caregivers), does the patient sit up and intend to get off the bed and etc. The computer vision component of the disclosed invention is the predominant sensor system used to determine positional state space.

The use of computer vision is both gross and specific in nature. Locations of the patients and caregivers, such as their standing/walking positions on the ground plane in a room are derived with low resolution while articulated motions of hands, facial expression and small item location and optical tags demand a more granular analysis that may focus on the detections/recognitions of certain movements of person body parts. Optical sensors combined with computer vision art make it possible to detect and track the location changes of patients, caregivers and/or objects over time from captured video imageries, while simultaneously recognizing specific actions of interest performed by the tracked individuals via analyzing the movements of body parts and interactions with objects in a clinical room environment.

Person detection and tracking algorithms and code receive inputs from multiple optical sensors, though the number of cameras is configurable and not necessarily fixed. Embodiments of the invention use a multi-camera, multi-person tracking system that includes a number of software component subsystems, which may be used to characterize physical state space of agents and objects in the clinical environment.

For example, one software component subsystem may be programmed to implement a foreground/background modeling and segmentation method, which identifies the regions of interest (ROIs) that could potentially contain people from captured video imageries. Also, a software component subsystem may be programmed to implement a geometry model-based person detection method, which relies on a geometry-based person shape model to explain the ROIs from foreground/background segmentation and report a set of candidate detections of persons.

Further, a software component subsystem may be programmed to implement an appearance classifier-based person detection method, which further validates above candidate detections using a dedicatedly trained person appearance classifier via machine learning approach. A software component subsystem may also be included to implement a person appearance modeling and matching method, which acquires person appearance signature from the detections, learns to adapt this signature model with new coming detection data.

Also, a software component subsystem may be programmed to implement a semantic scene model that may define the locations of walls, and locations/zones where medical equipment and furniture, fluid dispenser, washbasins, doors, windows, cart-based medical equipment, various items such as phones, trays, bed settings, optical or IR tags and garbage receptacles, are located in a clinical room environment.

Still further, a software component subsystem may be programmed to implement an automated object detection and localization method from video imageries, which assists in defining clinical room objects for above semantic scene model. A software component subsystem may also be included to implement a multi-camera, multi-person tracking methodology, which uses the outputs from aforementioned components, produces the filtered/smoothed trajectory of each tracked individual, and maintains track fidelity. A software component subsystem also may be programmed to implement a person type recognition method, which classifies a tracked person into predefined person type categories, such as doctors, nurses, patients, visitors, and/or others, etc. As another example, a software component subsystem may be programmed to implement a person-object interaction detection method, which senses a possible person-object interaction through a geometry measure between the tracked person trajectory and semantically defined object zone.

Figure 15:
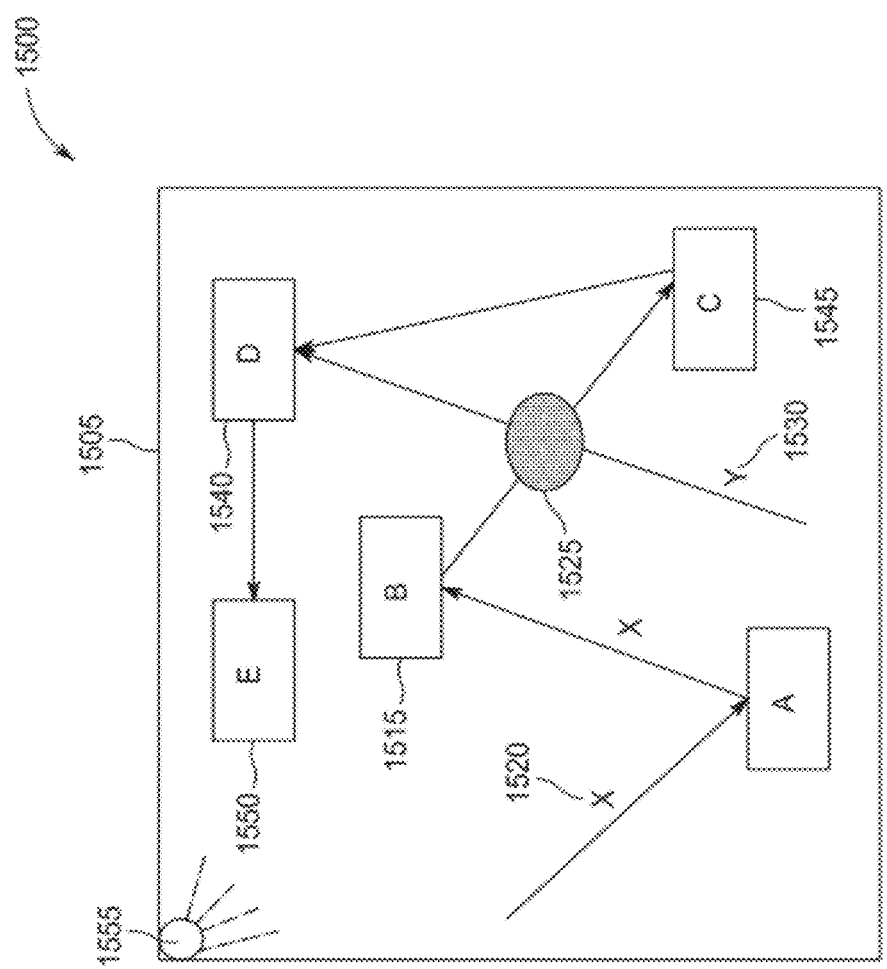
FIG. 15 is an exemplary schematic of a crossing event illustrating a cause for uncertainty.

A key characteristic of the disclosed system is that it reasons with spatiotemporal events by its ability to deal with uncertainty in the monitored information and yet create inferences that are robust. One source of uncertainty arises from ambiguities in sensing caused by practitioners crossing paths. For the computer vision system, this leads to uncertainty arising from multiple possible scenarios that cover all possibly interpretations after the crossing event happens, as illustrated through an example in FIG. 15, which is an exemplary schematic 1500 of a crossing event illustrating a cause for uncertainty. The range of optical sensors is given room geometries and the ability or desirability to mount more than a certain number of cameras. Movement in the monitored environment may be such that enough unique line of sight is lost, for example as two people cross or hug, that acceptable differentiation between the two is lost. Acceptable differentiation is a setting available in the system. It is then more uncertain what object or agent is which, relative to the certainty achieved up to the instant the loss of differentiation occurred.

Practitioners X 1520 and Y 1530 are both present in the room 1505 and the interesting zones in the room are illustrated as zone A 1510, zone B 1515, zone C 1545, zone D 1540 and zone E 1550. As shown, both practitioners X 1520 and Y 1520 cross the region indicated by the dark ellipse 1525 at the same point in time. As a result, all inferences about which agent causes the subsequent zone entries are uncertain. In other words, the entry-event for zone C 1545 (or zone D 1540 and zone E 1550) could have been caused by either of the two practitioners in the room since the sensing system 1555 cannot resolve the situation deterministically. To further the explanation, suppose the protocol requires any visit to zone C 1545 to be preceded by a visit to zone B 1515. Then, all interpretations where it was practitioner X 1520 who caused the zone C 1545 entry-event are safe, while alternative interpretations that have practitioner Y 1530 causing the zone C 1545 entry-event are protocol breaches. The ability to deterministically infer whether or not a breach has occurred becomes impossible.

By using additional processing within the sensing system to better resolve the ambiguity, the AI engine is then able to deal with state information that is uncertain. The AI reasoning engine overcomes precision challenges by maintaining probabilistic information that processes practitioner locations as probability distributions from the point where such uncertainty creeps into the system. According to one embodiment, the AI engine uses Bayesian updating to keep track of the location-distributions and converts those into likelihood functions of protocol breaches.

In instances when there is no explicit, domain-specific protocol definition, but the protocols are inferred from spatiotemporal events that have been sensed in the environment, the protocol discovery engine is used. A domain expert may identify instances of protocol breaches by looking at the event-list and tagging those that lead to a breach. The protocol discovery engine makes use of the tagged event-list to discover explicit protocol definition. This creates a rule-based representation of a state transition network that when instantiated would automatically detect the breaches consistent with the expert.

Figure 16:
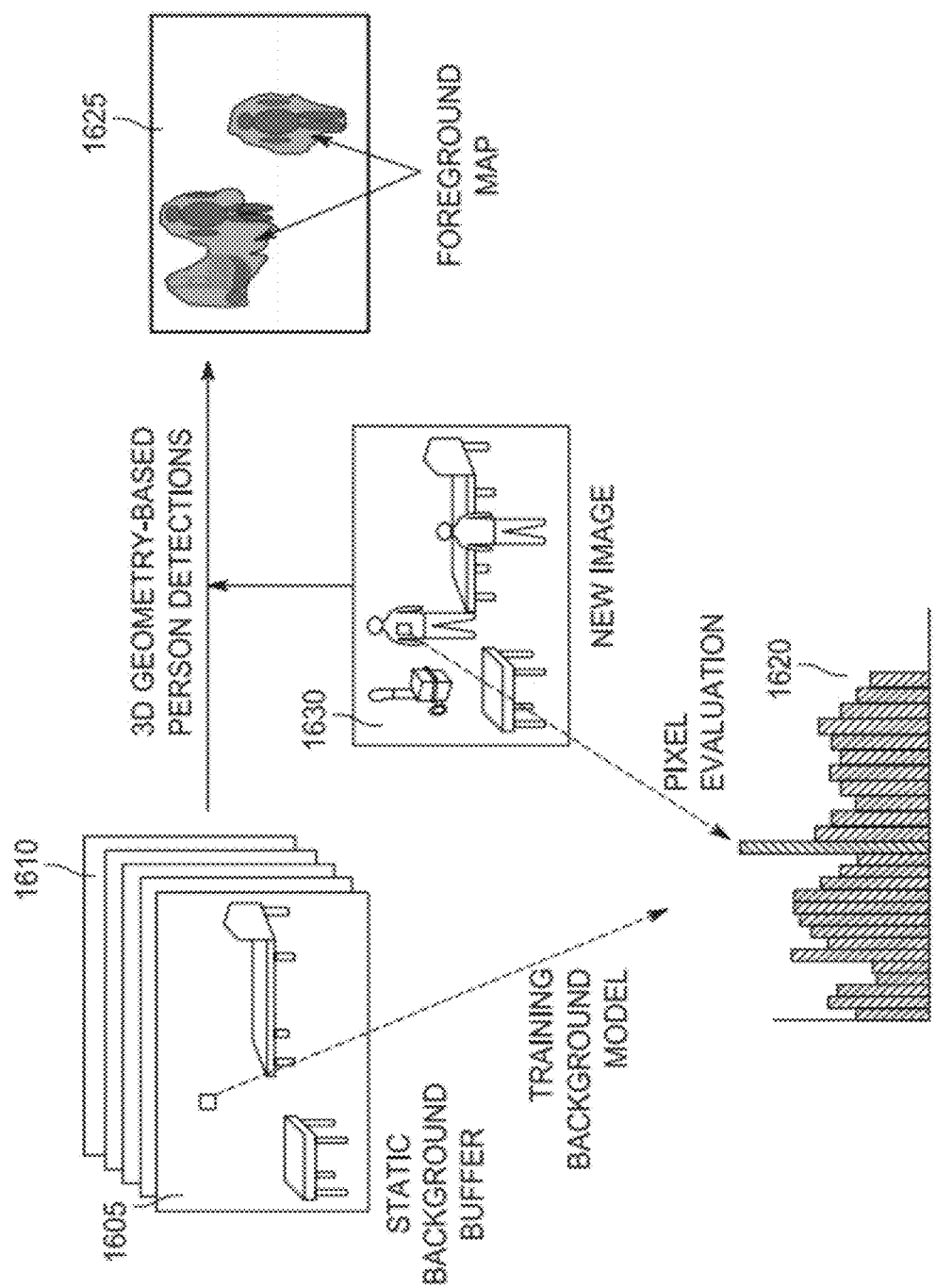
FIG. 16 is a schematic of foreground and background modeling and segmentation for use with embodiments of the invention.

Foreground/background modeling and segmentation is conceptualized in FIG. 16. Many instances of motion and identification of objects and agents are determined by calculating what has changed in scenes using data obtained from optical sensing. Backgrounds are stable over time and thus changes, such as the movement of an agent in the scene, may be made clear by subtracting the static background from the scene, thereby rendering the changing image as an item of interest that can be further classified until such time as it is identified and given ontological meaning. According to one embodiment, the scene is calculated pixel by pixel. The disclosed real-time person detection and tracking system 1600 consumes multiple camera inputs in fixed positions 1605, and person detection algorithms are executed independently on each camera view on a per-frame basis. Since the cameras are fixed, a pre-processing step based on foreground/background modeling and segmentation is employed to filter out stationary regions 1610 in the scene from further analysis. The system models the stationary background scenes using a per-pixel based grayscale/color histogram model 1620, which is learned continuously online. Any legitimate foreground regions, such as walking people and medical equipment 1630, that show significant different color patterns from the background model are extracted for further evaluation 1625.

Figure 17:
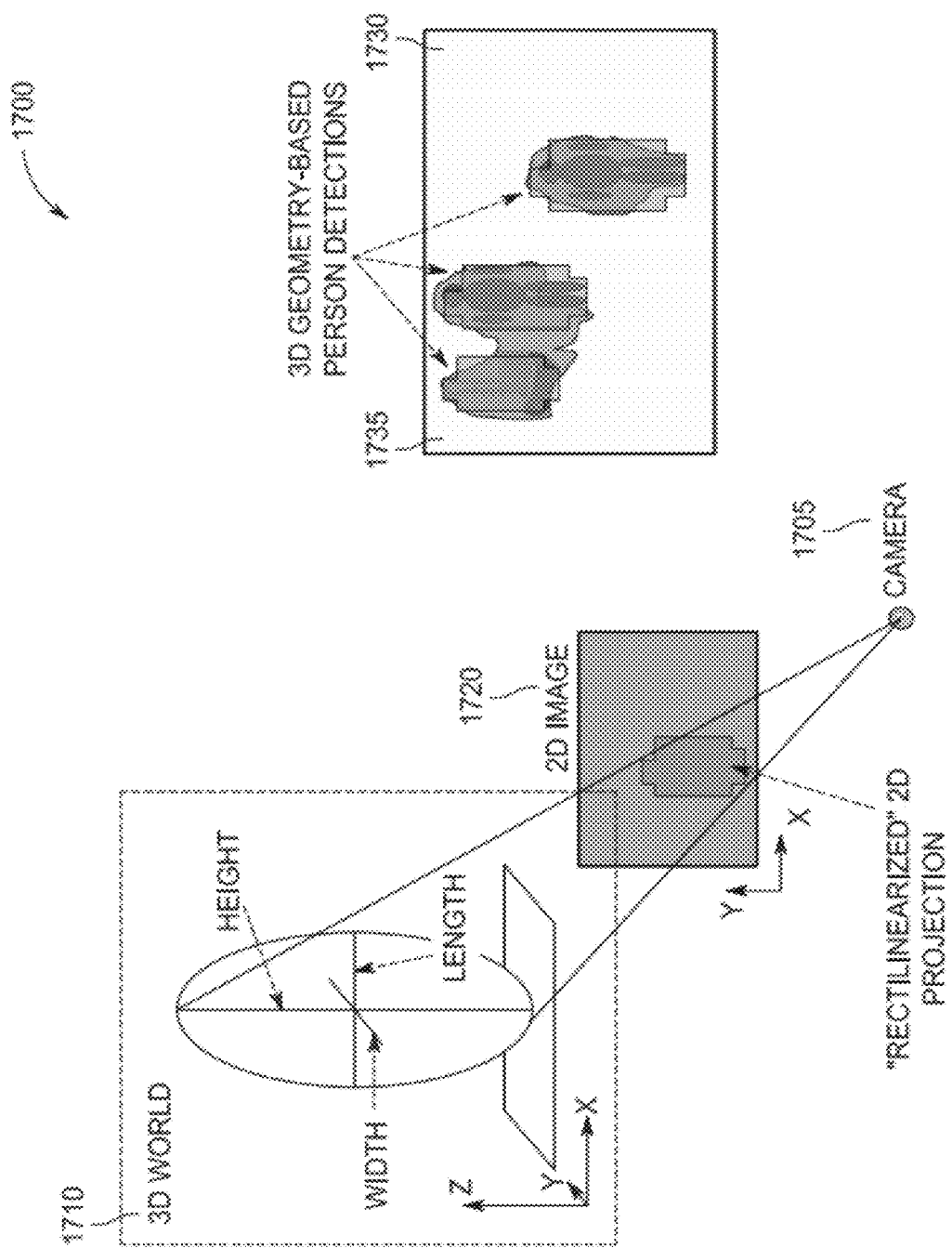
FIG. 17 is a schematic of a three-dimensional geometry-based person detection for use with embodiments of the invention.

FIG. 17 is a schematic of a three-dimensional geometry-based person detection system 1700 for use with embodiments of the invention. The item of interest, such as that produced from the foreground/background modeling and segmentation in FIG. 16, is desired to be identified. Determining what or who the specific agent that is detected is achieved by characterizing physical X-Y measures in a 2D space using one camera sensor or X-Y-Z in 3D using more than one camera. Cameras or optical sensors 1705 of system 1700 operate in a calibrated fashion, where the correspondence between the 3D world coordinate system 1710 and 2D image spaces 1720 can be established. Hence, a detailed 3D human body model may be crafted based on the physical dimension of a human and stands on the ground plane. The model's projection onto the image plane can be used to explain the extracted foreground regions and nominate a hypothesized set of ground plane locations that may be occupied by people 1730. Further validation is still needed to remove the hypotheses 1735 where the foreground shape does look like person but it is actually not.

Figure 18:
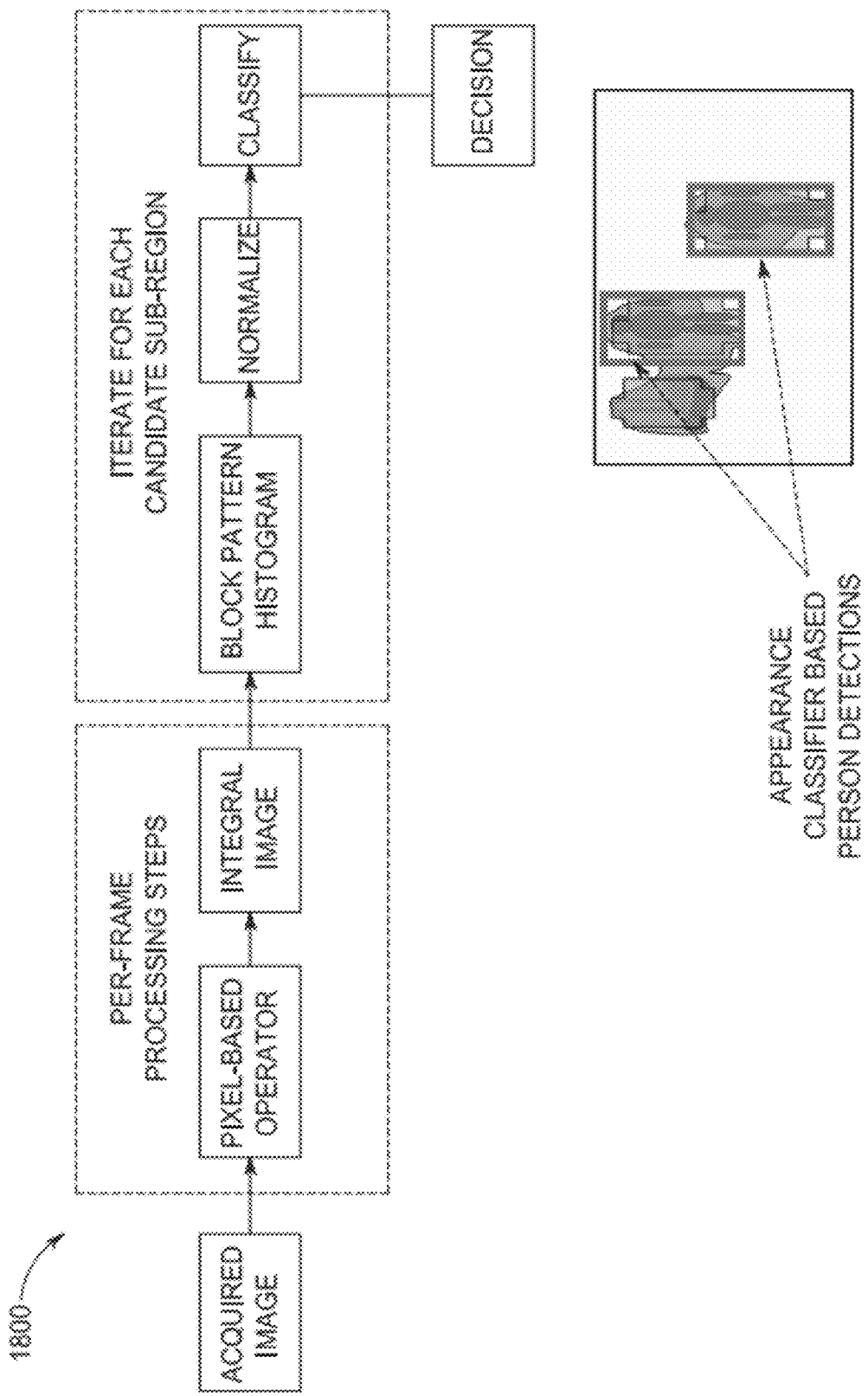
FIG. 18 is a flowchart for an appearance classifier-based person detection, in accordance with an embodiment of the invention.

FIG. 18 illustrates a flowchart 1800 for an appearance classifier-based person detection (HOG), in accordance with an embodiment of the invention. Appearance classifier-based person detection (HOG) may be achieved as depicted in FIG. 18 for each acquired image frame. Areas of interest are identified by the accumulation of relative pixel orientations and fitted to reference patterns for classification. People, when observed in the imageries, present certain unique feature patterns that make them distinguishable from other objects. Such a feature set can be discovered and learned using a machine learning approach from a large pool of feature space, which may include feature types such as gradient-orientation features, wavelet features, blob features, covariance features, and binary pattern features, as examples. The HOG method operates on these carefully selected yet efficiently computed features, and manages to learn a dedicated classification engine, which is capable of validating the existence of a person given the feature responses collected over a nominated window from 3D geometry-based person detection.

Depending on the types of persons being tracked by the system, such as caregiver, patient, and/or visitor, patient safety protocols may be tailored and enforced in a slightly different way. Thus, it is desired for the system to be capable of recognizing the person type. People may show slightly or dramatically different appearances, depending on the clothes they are wearing. Caregivers could look similar because of their identical uniforms. From computer vision perspective through discriminative learning paradigm, however, appearance signature models of different caregivers, for example, modeled by a histogram representation in some feature space, may still be learned to capture the appearance nuisance. The appearance signature modeling using machine-learning method can be applied here to learn the unique aspect of each person type. Accordingly, the learning method can leverage a large set of training data and build a person type recognizer in an offline manner. The learned appearance models will then be able to help establish the correspondence of person detections from successive video imageries by appearance matching, which is used for tracking people in this clinical environment. The model is also capable of performing self-adaptation with new coming data that has been assigned to it to allow the modeling of appearance changes of an individual.

Figure 19:
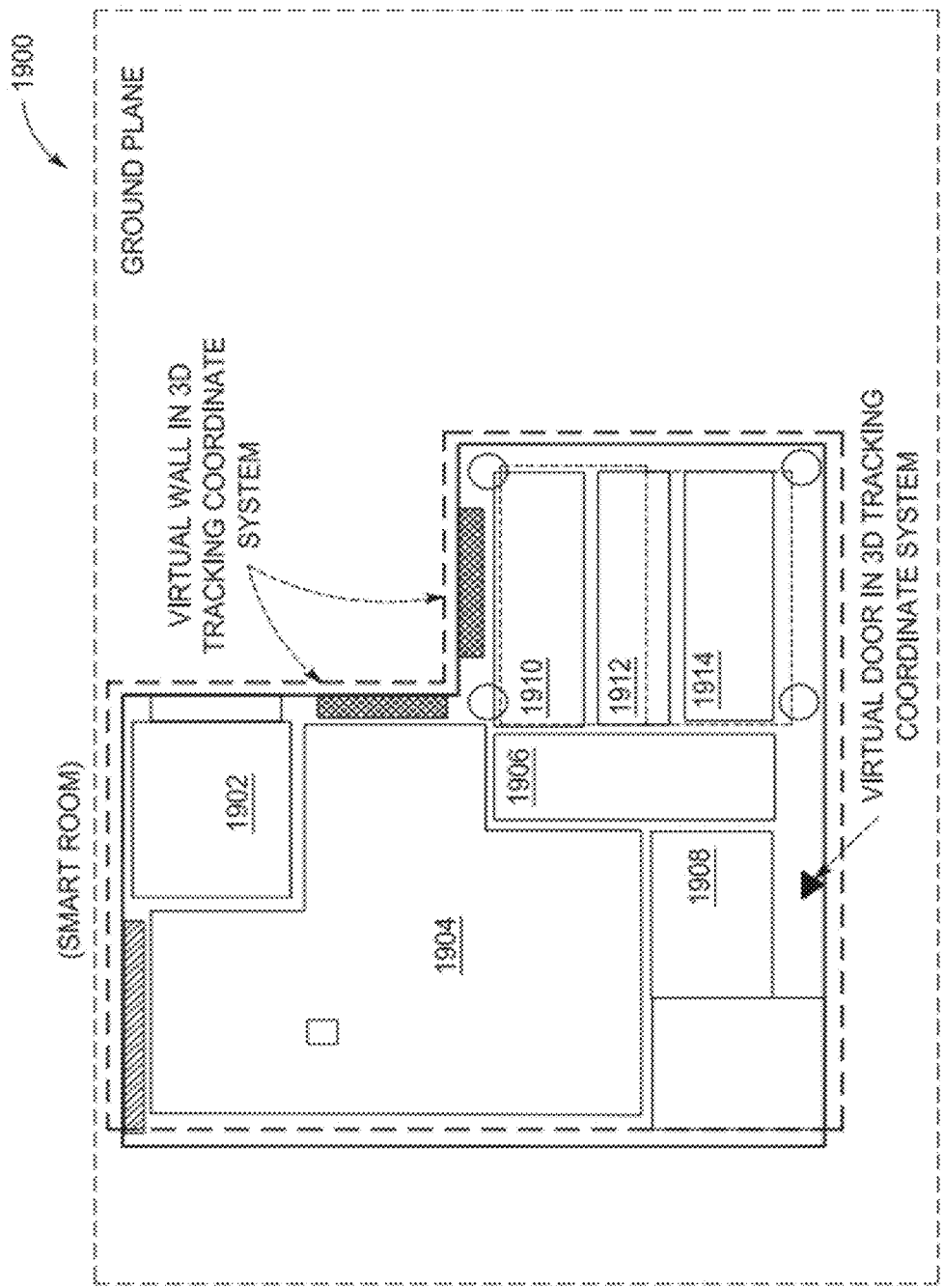
FIG. 19 is a schematic of a scene model and semantic zone definition in a patient room, in accordance with an embodiment of the invention.

FIG. 19 is a schematic 1900 of a scene model and semantic zone definition in a patient room, in accordance with an embodiment of the invention. Scene model and semantic zone definition in patient room is used to derive and communicate clinical context by virtue of what zone an object or agent is in. Zones 1902-1914 are configurable and tie to explicit protocol meaning depending upon the geo-spatial trail of agents traversing zones and the absolute zone location. An example being the logical determination that an agent must be physically in hand washing zone 1902 in order to have washed their hands (which event is only valid if done within that zone, not before entering the monitored space). All height information is projected onto a ground plane in the illustrated embodiment. 3D information is preferentially utilized in addition to semantic zones in other components of the system when more than one optical sensor is deployed.

The monitored space may be characterized and/or configured by the system to determine where the geo-spatial locations of zones are by incorporation of active feedback with monitored calibration device. An example embodiment is a beaconing device such as a wand or computer screen generating patterns that are directed from the system to capture a geospatial location for calibration purposes.

Clinical room is a physical indoor unit, where patient bed, hand dispenser/washbasins, medical equipment, etc., are placed in different locations. Analogically, a similar cartoon like 3D representation of the room can be constructed in a computer generated virtual world. The position of each room object in this virtual space can be either pre-selected manually, or determined automatically in a system online fashion, thus allowing their locations to be changed, for example a caregiver can move the patient bed. The detected persons from video imageries are also cast into this virtual space based on his/her estimated ground plane locations, and their spatial proximities to each of the room objects in the virtual space can thus easily be measured.

According to one embodiment, a large set of coded optical tags that can be readily detected and recognized using the video sensors are used to identify objects. Any combination of fixed objects such as doors and washbasins are labeled with these tags. In addition, dynamic objects, such as ventilator and patient bed, are labeled in a similar fashion. Each optical tag will code a unique pattern that can be distinguished using computer vision algorithms. Hence, by scanning the video imageries, the location of each object and its object type can both be uniquely determined.

Figure 20:
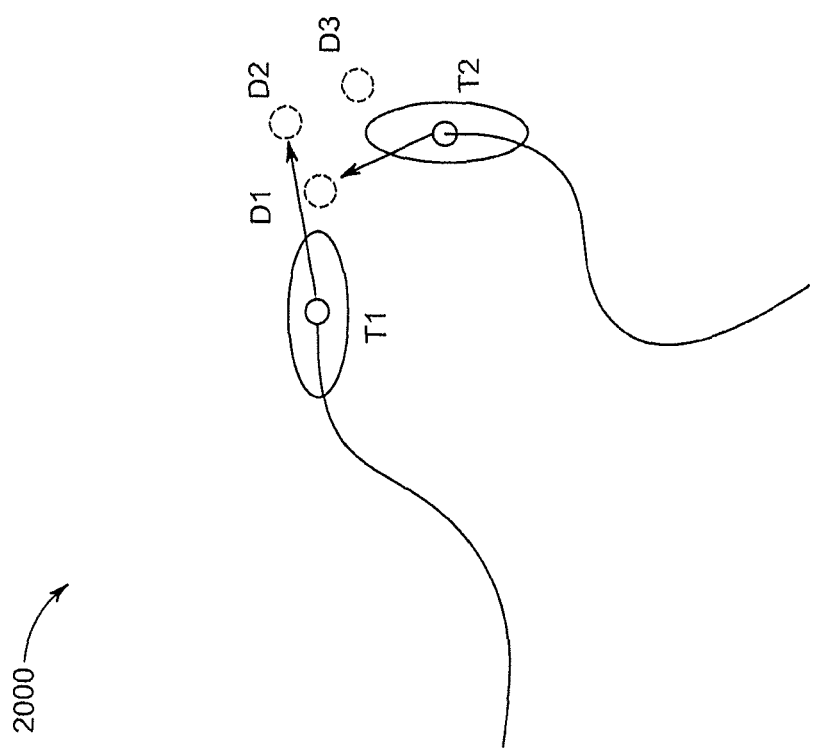
FIG. 20 is a schematic of a multi-camera, multi-person tracking system useable with the scene model and semantic zone definition of FIG. 19 according to various embodiments of the invention.

Referring to FIG. 20, a schematic of a multi-camera, multi-person tracking system 2000 is illustrated, according to an embodiment of the invention. The multi-camera, multi-person tracking system 2000 is useable with the scene model and semantic zone definition of FIG. 19 to differentiate agents in the monitored space by the incorporation of a number of other engines (such as Appearance, Zone and 3D geometry classifiers) into an association matrix for comparative classification. A most likely association is made and then published on the information broker for consumption by the subscribing protocol reasoning engine(s). The multi-person tracking in one embodiment is performed in a centralized fashion once person detections from each camera sensor are received and time ordered. Each newly detected person will be assigned with a new tracker with a unique tracker ID that operates on the ground plane in the aforementioned virtual semantic scene space. The data associations between the maintained trackers and detected persons rely upon a well-defined distance metric between these two, and it is quantified by a scoring system that is composed of three terms: appearance matching distance, ground plane distance, and classification score. The trajectory filtering/smoothing of each tracker is also performed on the ground plane in such a centralized fashion, enabling the system to provide continuous meta-data stream in the form of person locations as a function of time. According to one embodiment, up to five persons may be simultaneously tracked in a room.

RFID tags may also be used in conjunction with the computer vision to aid in identifying individuals. For example, a healthcare provider may wear an RFID tag. Upon entry into a patient's room, the computer vision system may access stored data corresponding to individual associated with the RFID tag and use that information to assist the computer vision system to more accurately track the individual.

The spatial proximity between tracked individual and a room object determines the feasibility of a person-object interaction. Only when a person walks close enough to an object, the further action, such as pressing hand dispenser and changing the ventilator, becomes possible. The proximity of an object can be quantified by a geometric zone defined to cover the object. Hence, to trigger the detection of a person-object interaction, the event of a tracked individual crossing and/or dwelling in an object zone must be detected, which is made possible because both the estimated trajectories of person trackers and object zone are defined in the virtual semantic scene model space.

Patient falling, turning, and/or ventilator change are typically associated with certain patterns of body movements (actions) either by patient him/herself or also with the involvement of caregivers. Hence, the enforcement of such related patient safety protocols, for example, patient fall prevention, pressure ulcer prevention, and ventilator-associated pneumonia prevention, use the capabilities of detecting these critical moments when these action patterns are taking place. From a computer vision and machine learning perspective, detecting the occurrences of such actions normally requires the discovery of a suit of related motion features in a fine granularity from imageries, and performs a classification/regression analysis on the features using an action specifically learned statistical model, trained over a representative set of sample data.

Embodiments of the present invention consider the motion features extracted in the space-time volumes of captured video imageries and potential other assisted sensors. The space-time motion features that can be used to characterize the training samples include, as examples, motion features from spatial-temporal filtering, motion features from sparse interest operators, occupancy measures from 3D image and depth sensors, positioning measures from bed load sensors (specifically for the recognition of patient actions in the bed), body articulation features from articulated human model fitting (location of head, arms, torso, legs, etc.), motion features from object detectors, positions of medical equipments (ventilator and medical gloves for ventilator-associated pneumonia prevention), and facial features from face model fitting and alignment (location of eyes, eyebrows, mouth, etc., for the measures of patient pain, distress and/or stroke).

If the classifier determines that a given set of space-time features is consistent with an action of interest, a detection and associated decision confidence are reported. Embodiments of the invention use various machine learning approaches, such as AdaBoost, for example, to construct such classifiers using a training paradigm (developers provide representative samples of both positive and negative actions). A potential list of action of interests that may lead to the detections of possible breaches in patient safety protocols may include, as examples, patient sits up and tends to get off the patient bed, caregiver picks up a medical device, a ventilator tube for instance, caregiver washes his/her hands using a hand washing basin, caregiver presses the hand dispenser and cleans his/her hands, and caregiver touches the patient.

Figure 21:
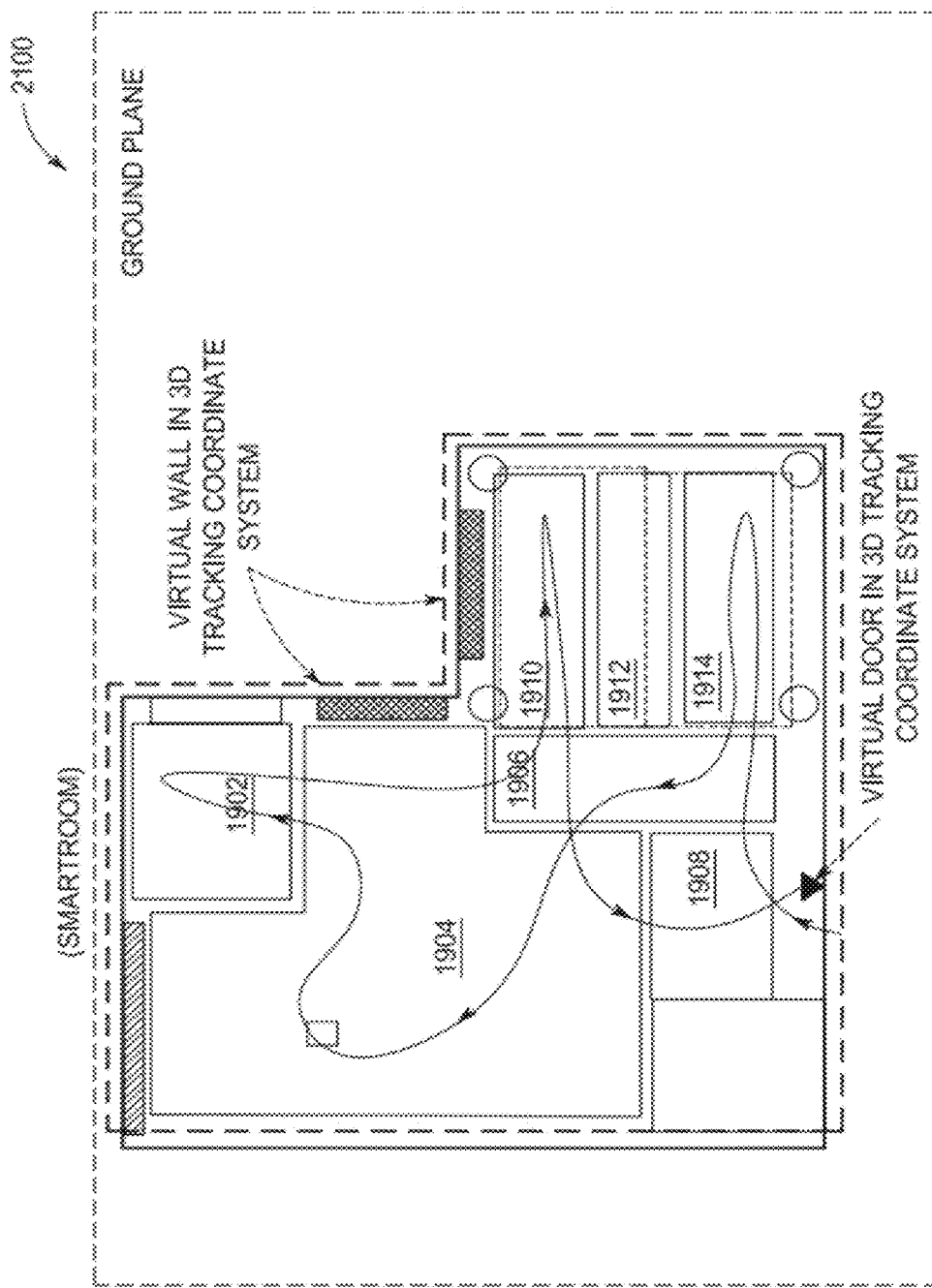
FIG. 21 is a schematic of a person-zone interaction event detection method useable with the scene model and semantic zone definition of FIG. 19 according to various embodiments of the invention.

FIG. 21 is a schematic of an exemplary person-zone interaction event detection 2100 useable with the scene model and semantic zone definition of FIG. 19. The person-zone interaction event detection 2100 is utilized to extract the benefit of trajectory and zone pattern in classifying the event activity of the agent, relative to the prescribed protocol. The reasoner will consume a sequence of temporally ordered person-zone interaction events and determine whether they match a desired pattern of events defined by the protocol. If the pattern is identified, then the reasoner determines that the protocol is adhered to. Depending on the level of adherence, reasoner may cause an alarm to be sounded or merely output a report to a database for later analysis. The stored data may be used for reverse data mining to identify patterns in the data. For example, if a high percentage of infections are occurring in a hospital at a particular time of day in a certain ward, data corresponding to that time and location may be analyzed to determine possible causes of the infections.

A technical contribution for the disclosed method and apparatus is that is provides for a computer implemented system and method for protocol adherence.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. An apparatus comprising:
an optical sensing system including:
a plurality of optical sensors configured to capture visual input in a monitored environment and generate optical sensor data characterizing a layout of the monitored environment, the plurality of optical sensors arranged to dynamically divide the monitored environment into a plurality of geo-spatial zones defining the layout, wherein each zone is associated with a task in a healthcare protocol to be monitored as part of a clinical workflow and wherein a crossing of an object between at least two zones is associated with a task in the healthcare protocol to be monitored;
a computer vision subsystem configured to utilize one or more of the plurality of optical sensors to transform the optical sensor data from the one or more optical sensors into a vector space identifying at least one of a location and trajectory of one or more monitored people and objects in the monitored environment;

an artificial intelligence engine configured to instantiate an augmented state transition network for each healthcare protocol to be monitored, the augmented state transition network encoding the protocol as states corresponding to protocol tasks and state transitions between tasks, the states representing the tasks and queued for monitoring, the state transitions based on a probability distribution associated with the at least one of a location and trajectory of one or more monitored people and objects in the vector space, wherein the artificial intelligence engine converts the probability distribution into a likelihood of protocol breach for the healthcare protocol to be monitored; and an information broker configured to publish messages from the augmented state transition network while the augmented state transition network is instantiated, the messages including the likelihood of protocol breach and information regarding the at least one of a location and trajectory of one or more monitored people and objects in the vector space; and a reasoning engine configured to subscribe to messages published by the information broker from the augmented state transition network, the reasoning engine to dynamically determine a protocol task violation based on deviation from a protocol state calculated using the messages, the reasoning engine triggering an alarm to report the deviation, wherein the reasoning engine is instantiated by a request from the clinical workflow and includes at least a protocol reasoning engine for the protocol, a task reasoning engine for protocol task, and a state reasoning engine for protocol state that work together to determine protocol compliance, and wherein the reasoning engine determines, using the messages and an ordered ontology for a healthcare domain, the protocol state formed from the messages using the ordered ontology based on i) a first state associated with an agent to perform an action, ii) a second state associated with an object that is a recipient of the action, and iii) a third state associated with an event that associates the action with the object and the agent, the ordered ontology enabling a processing of the protocol state and a comparison of the protocol state to identify the deviation based on an illegal state transition.

2. The apparatus of claim 1, wherein the optical sensing system and the reasoning engine are to be hosted in a message brokered computing environment.

3. The apparatus of claim 1, wherein one or more of the plurality of optical sensors is to identify an optical pattern on at least one of the monitored people and objects.

4. The apparatus of claim 3, wherein one or more of the plurality of optical sensors is to read dynamic signals produced on the display of a monitored object.

5. The apparatus of claim 1, wherein the augmented transition network is active while a monitored person is in the monitored environment and wherein the artificial intelligence engine destroys the instantiation of the augmented transition network when the monitored person has left the monitored environment based on information from one or more of the optical sensors.

6. The apparatus of claim 1, wherein proximity of a monitored object or person can be quantified by a geo-spatial zone defined to cover a volume of the monitored object or person.

7. The apparatus of claim 6, wherein an interaction between a first monitored object or person and a second monitored object or person is detected based on interaction between a first geo-spatial zone associated with the first monitored object or person and a second geo-spatial zone associated with the second monitored object or person.

8. The apparatus of claim 1, wherein at least one of the optical sensors includes a camera.

9. The apparatus of claim 1, wherein information captured from the one or more optical sensors is used to adjust a lighting level in the monitored environment.

10. The apparatus of claim 1, wherein the alarm includes at least one of audible feedback, visual feedback, or text-based feedback.

11. A non-transitory, computer-readable medium including instructions which, when executed by a processor, configure the processor to implement an apparatus comprising:

an optical sensing system including:
a plurality of optical sensors configured to capture visual input in a monitored environment and generate optical sensor data characterizing a layout of the monitored environment, the plurality of optical sensors arranged to dynamically divide the monitored environment into a plurality of geo-spatial zones defining the layout, wherein each zone is associated with a task in a healthcare protocol to be monitored as part of a clinical workflow and wherein a crossing of an object between at least two zones is associated with a task in the healthcare protocol to be monitored;

a computer vision subsystem configured to utilize one or more of the plurality of optical sensors to transform the optical sensor data from the one or more optical sensors into a vector space identifying at least one of a location and trajectory of one or more monitored people and objects in the monitored environment;

an artificial intelligence engine configured to instantiate an augmented state transition network for each healthcare protocol to be monitored, the augmented state transition network encoding the protocol as states corresponding to protocol tasks and state transitions between tasks, the states representing the tasks and queued for monitoring, the state transitions based on a probability distribution associated with the at least one of a location and trajectory of one or more monitored people and objects in the vector space, wherein the artificial intelligence engine converts the probability distribution into a likelihood of protocol breach for the healthcare protocol to be monitored; and an information broker configured to publish messages from the augmented transition network while the augmented state transition network is instantiated, the messages including the likelihood of protocol breach and information regarding the at least one of a location and trajectory of one or more monitored people and objects in the vector space; and a reasoning engine configured to subscribe to messages published by the information broker from the augmented state transition network, the reasoning engine to dynamically determine a protocol task violation based on deviation from a protocol state calculated using the messages, the reasoning engine triggering an alarm to report the deviation, wherein the reasoning engine is instantiated by a request from the clinical workflow and includes at least a protocol reasoning engine for the protocol, a task reasoning engine for protocol task, and a state reasoning engine for protocol state that work together to determine protocol compliance, and wherein the reasoning engine determines, using the messages and an ordered ontology for a healthcare domain, the protocol state formed from the messages using the ordered ontology based on i) a first state associated with an agent to perform an action, ii) a second state associated with an object that is a recipient of the action, and iii) a third state associated with an event that associates the action with the object and the agent, the ordered ontology enabling a processing of the protocol state and a comparison of the protocol state to identify the deviation based on an illegal state transition.

12. The computer-readable medium of claim 11, wherein the optical sensing system and the reasoning engine are to be hosted in a message brokered computing environment.

13. The computer-readable medium of claim 11, wherein one or more of the plurality of optical sensors is to identify an optical pattern on at least one of the monitored people and objects.

14. The computer-readable medium of claim 13, wherein one or more of the plurality of optical sensors is to read dynamic signals produced on the display of a monitored object.

15. The computer-readable medium of claim 11, wherein the augmented transition network is active while a monitored person is in the monitored environment and wherein the artificial intelligence engine destroys the instantiation of the augmented transition network when the monitored person has left the monitored environment based on information from one or more of the optical sensors.

16. The computer-readable medium of claim 11, wherein proximity of a monitored object or person can be quantified by a geo-spatial zone defined to cover a volume of the monitored object or person.

17. The computer-readable medium of claim 16, wherein an interaction between a first monitored object or person and a second monitored object or person is detected based on interaction between a first geo-spatial zone associated with the first monitored object or person and a second geo-spatial zone associated with the second monitored object or person.

18. The computer-readable medium of claim 11, wherein at least one of the optical sensors includes a camera.

19. The computer-readable medium of claim 11, wherein information captured from the one or more optical sensors is used to adjust a lighting level in the monitored environment.

20. The computer-readable medium of claim 11, wherein the alarm includes at least one of audible feedback, visual feedback, or text-based feedback.

* * * * *